United States Patent [19]

Stoddart et al.

[11] Patent Number: 4,570,638

[45] Date of Patent: Feb. 18, 1986

[54] METHOD AND APPARATUS FOR SPECTRAL TRANSMISSIBILITY EXAMINATION AND ANALYSIS

[75] Inventors: Hugh F. Stoddart, Groton, Mass.; Gary D. Lewis, St. Clair Shores, Mich.

[73] Assignee: Somanetics Corporation, St. Clair Shores, Mich.

[21] Appl. No.: 542,022

[22] Filed: Oct. 14, 1983

[51] Int. Cl.$^4$ ................................................ A61B 5/00
[52] U.S. Cl. ............................................................ 128/665
[58] Field of Search ................ 128/665, 666, 633, 664

[56] References Cited

U.S. PATENT DOCUMENTS

| | | | |
|---|---|---|---|
| 738,707 | 9/1903 | VanNort | 362/280 |
| 2,358,992 | 9/1944 | Millikan | 356/41 |
| 2,414,747 | 1/1947 | Kirschbaum | 128/204.23 |
| 2,423,855 | 7/1947 | Smaller | 356/41 |
| 2,437,916 | 3/1948 | Greenwald | 128/665 |
| 2,439,857 | 4/1948 | Millikan | 356/41 |
| 2,442,462 | 6/1948 | Kirschbaum | 128/633 |
| 2,475,132 | 7/1949 | Ergen | 318/678 |
| 2,640,389 | 6/1953 | Liston | 128/633 |
| 2,685,815 | 8/1954 | Mayne | 128/633 |
| 2,706,927 | 4/1955 | Wood | 356/41 |
| 2,760,485 | 8/1956 | Adelman | 128/633 |
| 2,790,438 | 4/1957 | Taplin et al. | 128/633 |
| 3,036,568 | 5/1962 | Stark | 128/664 |
| 3,123,066 | 3/1964 | Brumley | 128/634 |
| 3,136,310 | 6/1964 | Meltzer | 128/634 |

(List continued on next page.)

FOREIGN PATENT DOCUMENTS

| | | | |
|---|---|---|---|
| 0484366 | 7/1975 | Australia | 128/633 |
| 3015 | 7/1979 | European Pat. Off. | 356/41 |
| 19478 | 11/1980 | European Pat. Off. | 318/678 |
| 23186 | 1/1981 | European Pat. Off. | 356/41 |
| 46601 | 3/1982 | European Pat. Off. | 128/645 |
| 2023318 | 12/1971 | Fed. Rep. of Germany | 128/633 |

(List continued on next page.)

OTHER PUBLICATIONS

IBM Technical Disclosure Bulletin, vol. 10, No. 3, Aug., 1967, "Stacker Selection System", by A. K. Brooks & C. J. Kellerman, pp. 225–226.
"MICR Automatic Gain Control", by R. W. Arnold, pp. 227–228.
"Biomedizinische Technik" (Germany) Band 17, 1972, No. 3, p. 93.
"Biomedizinische Technik" (Germany) Band 18, 1973, No. 4, p. 142.
"IEEE Transactions on Biomedical Engineering", vol.

(List continued on next page.)

Primary Examiner—John Doll
Assistant Examiner—Anthony McFarlane
Attorney, Agent, or Firm—Price, Heneveld, Huizenga & Cooper

EXEMPLARY CLAIM

1. Apparatus for obtaining optical response data from selected body portions of individual subjects indicative of the intrinsic internal physiological state of tissue within such body portions, comprising: a manually-manipulatable test instrument having at least first and second component members mounted for movement relative to one another and support means disposed therebetween for holding such members in selected mutually spaced relative positions; said first component member including light source means for emitting selected light from said first member; said first component member being adapted to fit closely against a selected body portion from which clinical data is desired to be obtained, in a manner to project said emitted light into the interior of such body portion; light-receiving means carried by at least said second component member for receiving at least part of the light projected into said selected body portion; said support means including position-variable elements for movement of one of said component members relative to the other to change the nominal optical distance between said source and said light-receiving means; means operatively coupled between said light source means and said light-receiving means for measuring the particular length of said nominal optical distance at various positions of said relative movement which effects change in such distance; and means for producing signals for computation representative of the nominal optical distance determined by said length-measurement means.

47 Claims, 16 Drawing Figures

U.S. PATENT DOCUMENTS

| | | | |
|---|---|---|---|
| 3,152,587 | 10/1964 | Ullrich et al. | 128/633 |
| 3,313,290 | 4/1967 | Chance et al. | 128/633 |
| 3,335,716 | 8/1967 | Alt et al. | 128/664 |
| 3,349,762 | 10/1967 | Kapany | 128/666 |
| 3,406,645 | 10/1968 | Zandman | 128/645 |
| 3,412,729 | 11/1968 | Smith, Jr. | 128/633 |
| 3,461,856 | 8/1969 | Polanyi | 128/633 |
| 3,511,227 | 5/1970 | Johnson | 128/666 |
| 3,517,999 | 6/1970 | Weaver | 356/32 |
| 3,527,932 | 9/1970 | Thomas | 128/23 |
| 3,602,213 | 8/1971 | Howell et al. | 128/2.05 P |
| 3,628,525 | 12/1971 | Polanyi et al. | 128/2.05 P |
| 3,672,352 | 6/1972 | Summers | 128/2 R |
| 3,674,013 | 7/1972 | Polanyi | 128/2.05 D |
| 3,677,648 | 7/1972 | Dorsch | 356/40 |
| 3,690,769 | 9/1972 | Mori | 356/41 |
| 3,704,706 | 12/1972 | Herczfeld et al. | 128/2 R |
| 3,710,011 | 1/1973 | Altemus et al. | 128/5.4 R |
| 3,734,091 | 5/1973 | Taplin | 128/142 |
| 3,748,471 | 7/1973 | Ross et al. | 250/333 |
| 3,769,963 | 11/1973 | Goldman et al. | 128/2 R |
| 3,769,974 | 11/1973 | Smart et al. | 128/633 |
| 3,777,738 | 12/1973 | Sugita et al. | 128/2 T |
| 3,787,119 | 1/1974 | Rybak | 356/73 |
| 3,814,081 | 6/1974 | Mori | 128/2 L |
| 3,822,695 | 7/1974 | Takayama | 128/2 L |
| 3,847,483 | 11/1974 | Shaw et al. | 356/41 |
| 3,881,481 | 5/1975 | Huele et al. | 128/2.05 V |
| 3,889,656 | 6/1975 | Krawitt | 128/2 R |
| 3,910,701 | 10/1975 | Henderson et al. | 128/625 |
| 3,958,560 | 5/1976 | March | 128/2.05 E |
| 3,963,019 | 6/1976 | Quandt | 128/2 T |
| 3,980,075 | 9/1976 | Heule | 128/205 T |
| 3,987,303 | 10/1976 | Stoft et al. | 250/343 |
| 3,993,047 | 11/1976 | Peek | 128/2.05 P |
| 4,013,067 | 3/1977 | Kresse et al. | 128/2.05 R |
| 4,014,321 | 3/1977 | March | 128/2 A |
| 4,015,595 | 4/1977 | Benjamin, Jr. | 128/2.05 V |
| 4,029,085 | 6/1977 | DeWitt et al. | 128/2 R |
| 4,030,485 | 6/1977 | Warner | 128/2 R |
| 4,041,933 | 8/1977 | Reichenberger | 128/2 E |
| 4,048,493 | 9/1977 | Lee | 250/205 |
| 4,073,292 | 2/1978 | Edelman | 128/214 E |
| 4,086,616 | 4/1978 | Catano et al. | 358/81 |
| 4,109,643 | 8/1978 | Bond et al. | 128/2 L |
| 4,109,647 | 8/1978 | Stern et al. | 128/2.05 L |
| 4,114,604 | 9/1978 | Shaw et al. | 128/2 L |
| 4,123,172 | 10/1978 | French | 356/188 |
| 4,157,708 | 6/1979 | Imura | 128/666 |
| 4,163,447 | 8/1979 | Orr | 128/666 |
| 4,166,695 | 9/1979 | Hill et al. | 356/28 |
| 4,167,331 | 9/1979 | Nielsen | 356/39 |
| 4,170,987 | 10/1979 | Anselmo et al. | 128/665 |
| 4,175,545 | 11/1979 | Termanini | 128/666 |
| 4,178,917 | 12/1979 | Shapiro | 128/665 |
| 4,183,360 | 1/1980 | Carlson et al. | 128/666 |
| 4,198,988 | 4/1980 | Cash, Jr. et al. | 128/666 |
| 4,202,339 | 5/1980 | Wirtzfeld et al. | 128/419 PG |
| 4,207,892 | 6/1980 | Binder | 128/665 |
| 4,212,306 | 7/1980 | Mahmud | 128/665 |
| 4,212,306 | 7/1980 | Mahmud | 128/665 |
| 4,213,462 | 7/1980 | Sato | 128/634 |
| 4,222,389 | 9/1980 | Rubens | 128/633 |
| 4,223,680 | 3/1979 | Jobsis | 128/633 |
| 4,236,526 | 12/1980 | Richard | 128/633 |
| 4,241,738 | 12/1980 | Lubbers et al. | 128/666 |
| 4,249,540 | 2/1981 | Koyama et al. | 128/666 |
| 4,253,447 | 3/1981 | Moore et al. | 128/6 |
| 4,253,744 | 3/1981 | Sawa | 351/16 |
| 4,259,948 | 4/1981 | Urban | 128/6 |
| 4,259,963 | 4/1981 | Huch | 128/635 |
| 4,261,344 | 4/1981 | Moore et al. | 128/6 |

FOREIGN PATENT DOCUMENTS

| | | | |
|---|---|---|---|
| 2053301 | 5/1972 | Fed. Rep. of Germany | 128/633 |
| 2263890 | 7/1973 | Fed. Rep. of Germany | 128/2.05 D |
| 2065515 | 3/1974 | Fed. Rep. of Germany | 128/2 R |
| 2430788 | 10/1975 | Fed. Rep. of Germany | 128/23 |
| 2538985 | 5/1976 | Fed. Rep. of Germany | 356/41 |
| 2517129 | 6/1976 | Fed. Rep. of Germany | 356/32 |
| 2641144 | 3/1977 | Fed. Rep. of Germany | 356/41 |
| 2741913 | 4/1978 | Fed. Rep. of Germany | 128/2 T |
| 2741981 | 4/1978 | Fed. Rep. of Germany | 250/333 |

(List continued on next page.)

OTHER PUBLICATIONS

BME-26, No. 7, Jul., 1979, p. 416, A Neonatal Fiberoptic Probe for Oximetry and Dye Curves.

"IEEE Transactions on Biomedical Engineering", vol. BME-23, No. 5, Sep., 1976, p. 391 & Title cover, Multiple Scattering Analysis of Retinal Blood Oximetry.

"IEEE Transactions on Biomedical Engineering", vol. BME-25, No. 1, Jan., 1978, p. 28, An Instrument to Measure Cutaneous Blood Flow Using the Doppler Shift of Laser Light.

"IEEE Transactions on Biomedical Engineering", vol. BME-22, No. 3, May, 1975, p. 183 & Title cover, The Choroidal Eye Oximeter, An Instrument for Measuring Oxygen Saturation of Choroidal Blood In Vivo.

"IEEE Transactions on Biomedical Engineering", vol. BME-26, No. 4, Apr., 1979, p. 220, Applications of Photoacoustic Spectroscopy to Problems in Dermatology Research.

The Waters Company Advertisement on X-350 Oximeter (Rochester, Minnesota).

"Medical & Biological Engineering", vol. 6, 1968 (U.K.), p. 409, Tissue Identification During Needle Puncture by Reflection Spectrophotometry.

"Medical & Biological Engineering", vol. 10, 1972 (U.K.), p. 385, A Light Emitting Diode Skin Reflectance Oximeter.

"Medical & Biological Engineering & Computing", vol. 18, No. 3, May, 1980, p. 265, Self-Stabilising System for Measuring Infrared Light Back-Scattered from Vaginal Tissue.

"Medical & Biological Engineering & Computing", Jan., 1980, p. 27, Spectrophotometric Monitoring of Arterial Oxygen Saturation in the Fingertip.

"Medical and Biological Engineering & Computing", (List continued on next page.)

U.S. PATENT DOCUMENTS

| | | | |
|---|---|---|---|
| 4,266,554 | 5/1981 | Hamaguri | 128/633 |
| 4,267,844 | 5/1981 | Yamanishi | 128/633 |
| 4,281,645 | 8/1981 | Jobsis | 128/633 |
| 4,286,602 | 9/1981 | Guy | 128/665 |
| 4,290,433 | 9/1981 | Alfano | 128/665 |
| 4,295,470 | 10/1981 | Shaw et al. | 128/634 |
| 4,305,398 | 12/1981 | Sawa | 128/633 |
| 4,312,357 | 1/1982 | Andersson et al. | 128/664 |
| 4,321,930 | 3/1982 | Jobsis | 128/633 |
| 4,331,132 | 5/1982 | Mukasa | 128/6 |
| 4,332,258 | 6/1982 | Arai et al. | 128/666 |
| 4,336,809 | 6/1982 | Clark | 128/665 |
| 4,339,954 | 7/1982 | Anson et al. | 73/657 |
| 4,344,438 | 8/1982 | Schultz | 128/634 |
| 4,350,163 | 9/1982 | Ford, Jr. et al. | 128/633 |
| 4,365,307 | 12/1982 | Tatsuwaki et al. | 364/557 |
| 4,370,986 | 2/1983 | Gebhart et al. | 128/716 |
| 4,380,240 | 4/1983 | Jobsis et al. | 128/633 |
| 4,446,871 | 5/1984 | Imura | 128/664 |
| 4,467,812 | 8/1984 | Stoller | 128/665 |
| 4,467,812 | 8/1984 | Stoller | 128/664 |
| 4,479,499 | 10/1984 | Alfano | 128/665 |
| 4,495,949 | 1/1985 | Stoller | 128/664 |
| 4,495,949 | 1/1985 | Stoller | 128/664 |
| 4,510,938 | 4/1985 | Jobsis et al. | 128/633 |

FOREIGN PATENT DOCUMENTS

| | | | |
|---|---|---|---|
| 2724543 | 12/1978 | Fed. Rep. of Germany | 128/2.05 V |
| 2726606 | 12/1978 | Fed. Rep. of Germany | 128/2 L |
| 2827488 | 2/1979 | Fed. Rep. of Germany | 128/2 T |
| 2823769 | 12/1979 | Fed. Rep. of Germany | 250/343 |
| 2947194 | 7/1981 | Fed. Rep. of Germany | 128/2 R |
| 2481917 | 11/1981 | France | 128/666 |
| 2517953 | 6/1983 | France | 128/634 |
| 149157 | 7/1981 | German Democratic Rep. | 128/633 |
| 54-129786 | 10/1979 | Japan | 128/2 R |
| 745646 | 2/1956 | United Kingdom | 128/2 A |
| 777651 | 10/1956 | United Kingdom | 356/188 |
| 2068537A | 8/1981 | United Kingdom | 128/665 |
| 2076963A | 12/1981 | United Kingdom | 128/2 L |
| 2092856A | 8/1982 | United Kingdom | 128/366 |
| 124701 | 12/1958 | U.S.S.R. | 128/666 |
| 0146905 | 7/1961 | U.S.S.R. | 128/666 |
| 0283670 | 10/1970 | U.S.S.R. | 128/634 |
| 0311618 | 8/1971 | U.S.S.R. | 128/665 |
| 0680725 | 8/1979 | U.S.S.R. | 128/666 |
| 0696378 | 11/1979 | U.S.S.R. | 128/666 |
| 696378 | 11/1979 | U.S.S.R. | 128/6 |
| 704598 | 12/1979 | U.S.S.R. | 128/635 |
| 786983 | 12/1980 | U.S.S.R. | 128/633 |
| 824995 | 4/1981 | U.S.S.R. | 128/633 |

OTHER PUBLICATIONS

Nov., 1979, p. 763, Backscattering of Light by Red Cell Suspensions.

"Medical & Biological Engineering & Computing", Mar., 1980, p. 250, Piosecond Laser Sterometry Light Scattering Measurements on Biological Material.

"Medical & Biological Engineering & Computing", vol. 17, No. 3, May, 1979, p. 419, Psiological Light-Emitting Diode Photocell Monitor.

"Medical & Biological Engineering & Computing", vol. 20, No. 1, Jan., 1982, p. 111, Development of an Optical Fibre Technique for He-Ne Laser Screening of Human Body and Its Comparison with the Integrating Sphere Method.

"Analytical Chemistry", vol. 52, No. 6, May, 1980, p. 864, Fiber Optic pH Probe for Physiological Use.

"Medical Instrumentation", vol. 9, No. 3 (May-Jun., 1975), p. 136, Continuous In Vivo Assessment of Arteriovenous Oxygen Difference Utilizing a Fiberoptic Catheter Oximeter.

"Biomedical Engineering & Computing", vol. 5, No. 11 (U.K.), Nov. 1970, p. 549.

"Medical Instrumentation", vol. 13, No. 4 (Jul.-Aug., 1979), p. 232, A Versatile Simultaneous Multifinger Photocell Plethysmography System for Use in Clinical and Occupational Medicine.

"Biomedical Engineering" (U.S.A.), vol. 12, No. 1, Jan.-Feb., 1978, (published 9/78), p. 20, Instrument for Measuring Microconcentrations of Indicator Dyes in Blood.

"Chest, 76", Jul. 1, 1979, p. 27, Fluorescence Bronchoscopy for Detection of Lung Cancer.

"Review of Scientific Instruments", vol. 51, No. 10, Oct., 1980, p. 1403, Endoscopic System for Simultaneous Visual Examination and Electronic Detection of Fluorescence.

"Hewlett-Packard Journal", vol. 28, No. 2, Oct. 1976, p. 2 & Title Cover Sheet, Continuous, Non-Invasive Measurements of Arterial Blood Oxygen Levels.

"Laser Electro Optic", No. 1, (1978), U.S.A., p. 22, A Non-Contract High Sensitivity Laser Stethoscope.

"Medicamundi", vol. 17, No. 1 (1972), Abstract & p. 7, The Principle Design and Features of a New Hb-Oximeter.

"The American Journal of Cardiology", vol. 49, Mar., 1982, p. 743, Simultaneous Measurement of Coronary Venous Blood Flow and Oxygen Saturation During Transient Alterations in Myocardial Oxygen Supply and Demand.

"SPIE", (Soc. Photo-Optical Instrumentation Engineering), vol. 211, (1979), p. 128, Subpicosecond Spectroscopic Techniques in Biological Materials.

"EDN" Sep. 20, 1980, vol. 25, No. 17, p. 69, Fitness and Health-Care Products Incorporate Advanced Electronics.

"1979" IEEE International Solid State Circuits Conference, Pennsylvania, Feb. 14-16, 1979, p. 202, Session XV: Solid-State Imaging and Biomedical Applications.

"Journal of Biomedical Engineering", vol. 4, No. 2, Apr., 1982, p. 142, An Infra-Red Reflectance System for Ambulatory Characterization of Left Ventricular Function.

"IEEE 1979 Frontiers of Engineering in Health Care Conference", Denver, Colorado, U.S.A., p. 209, Session 9: Pulse Rate Monitor.

"Vestnik Dermatologi i Venerologii", (Russian), vol. 35, Jun., 1961, pp. 17-20 & 1st sheet of translation The Role of the Luminescence Method in the Diagnosis of Some Dermatoses.

"Proceedings of the 26th Annual Conference on Engi- (List continued on next page.)

OTHER PUBLICATIONS neering in Medicine & Biology", Minneapolis, Minnesota, Sep. 30–Oct. 4, 1973, p. 276, Improved Extracorporeal Reflectance-Oximeter.

"Proceedings of the Thirteenth ISA Aerospace Instrumentation, Symposium", San Diego, California, Jun. 13–Jun. 16, 1967, p. 489 & Title Cover, New Horizons in Biomedical Instrumentation.

"IRE" Transactions on Medical Electronics, Jul., 1958, Contents page and Copyright Notice, note p. 34, article on Oximetry by W. Paul.

"IEEE Transactions on Biomedical Engineering", vol. BME-24, No. 2, Mar., 1977; A proposed Miniature Red/Infrared Oximeter Suitable for Mounting on a Catheter Tip.

"Medical Instrumentation", vol. 7, No. 4, Sep.–Oct., 1973, p. 262, Oxygen Saturation Monitor for Extra-Corporeal Circulation Applications.

"IEEE Transactions on Biomedical Engineering", vol. BME-25, No. 1, Jan., 1978, p. 94, An Electronic Circuit for Red/Infrared Oximeters.

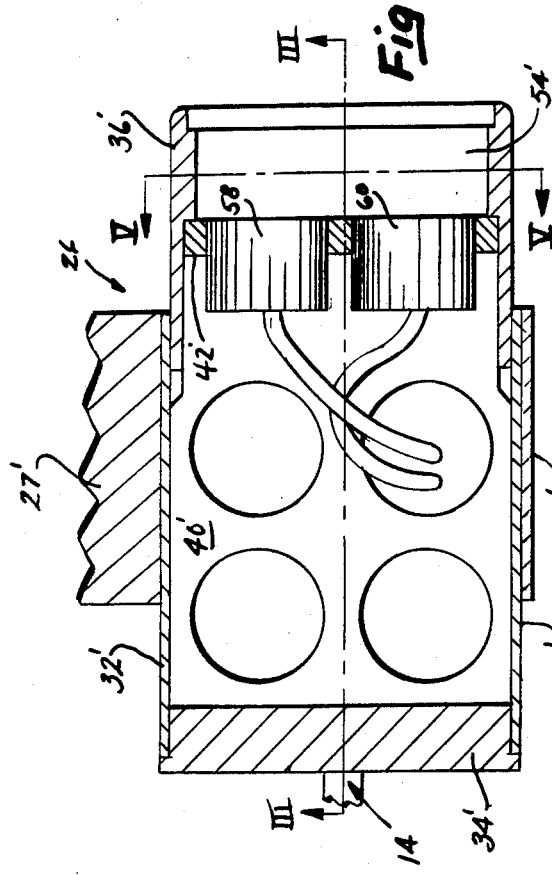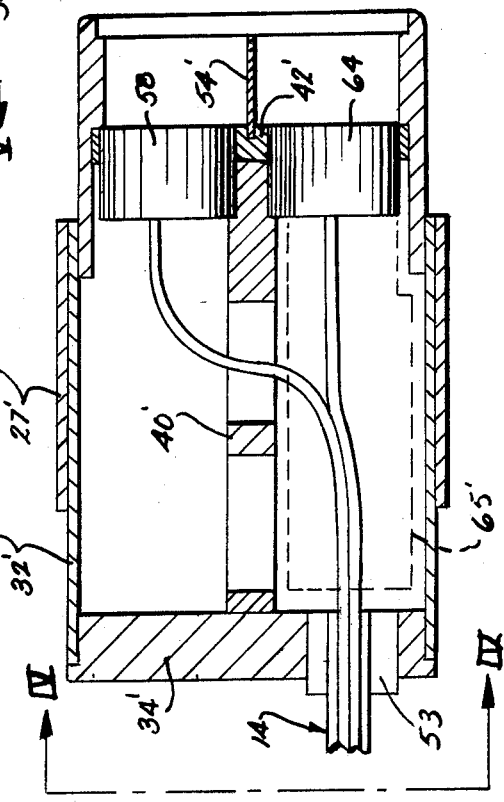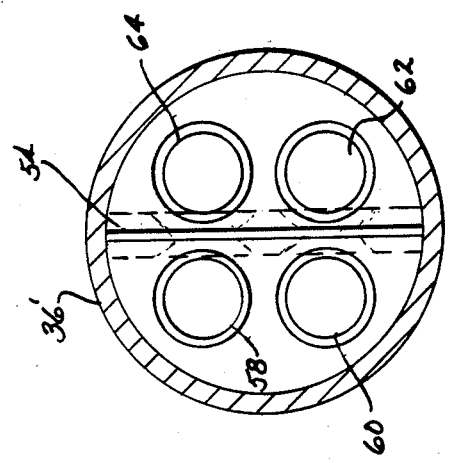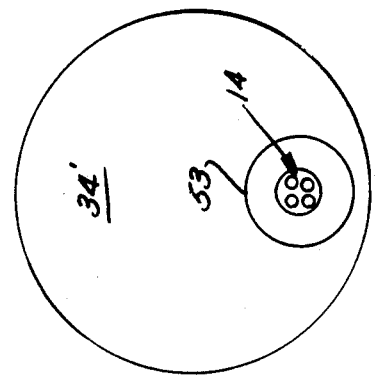

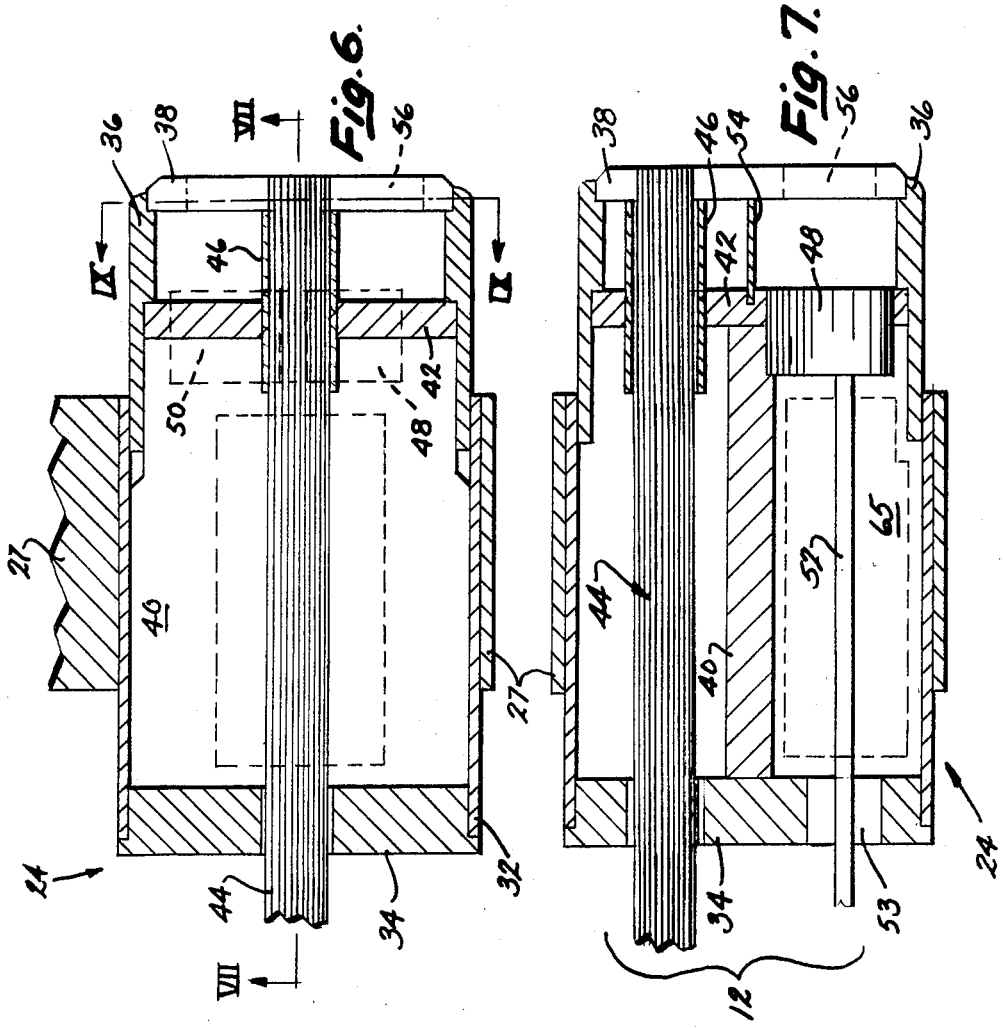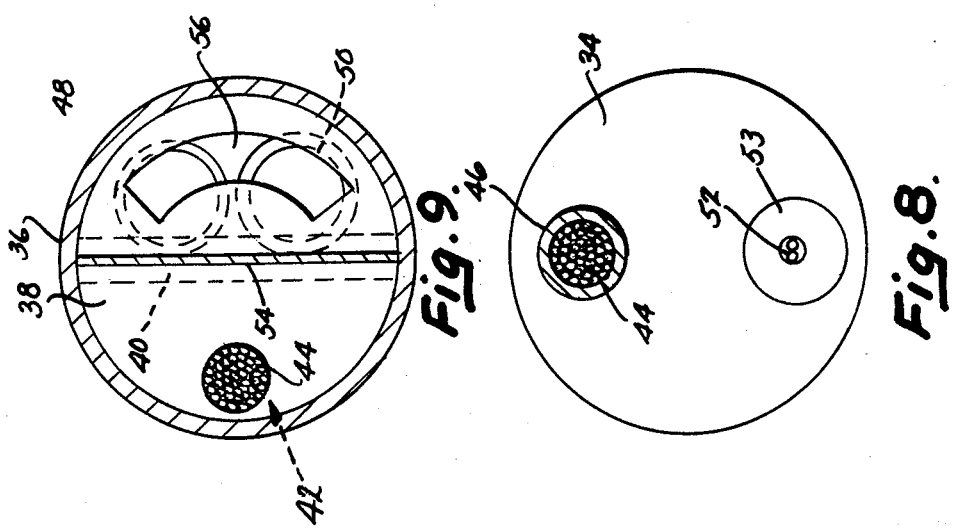

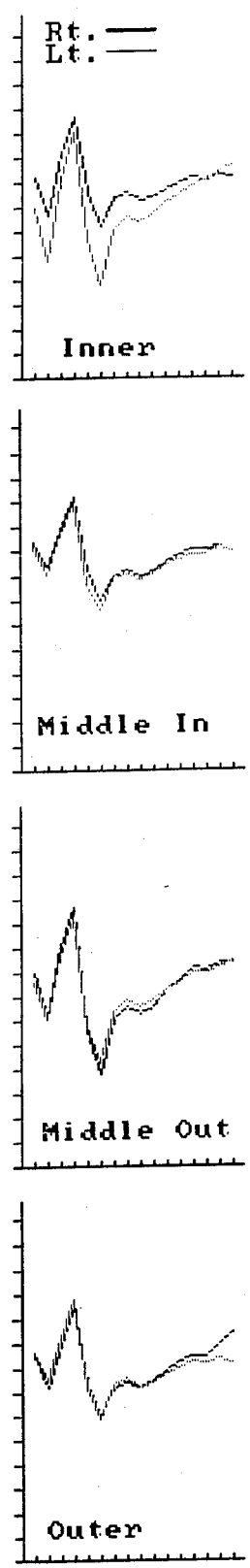
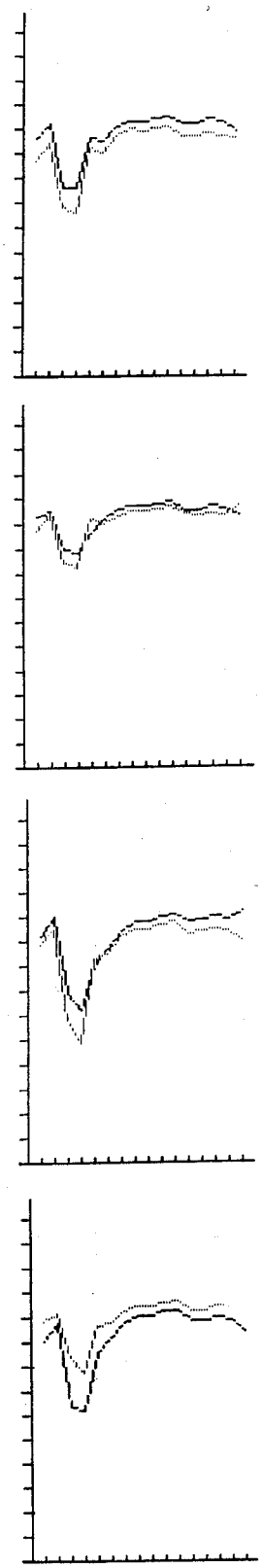
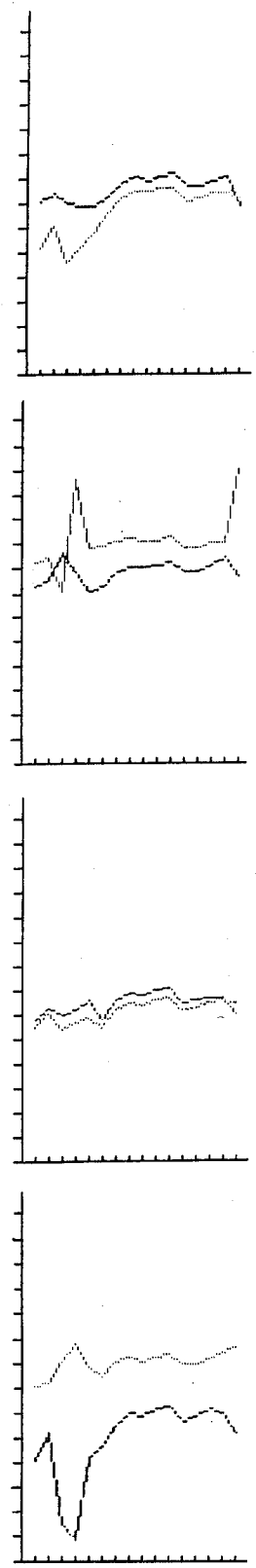
Fig. 14a.   Fig. 14b.   Fig. 14c.
Fig. 14.

METHOD AND APPARATUS FOR SPECTRAL TRANSMISSIBILITY EXAMINATION AND ANALYSIS

TECHNICAL FIELD

This invention relates generally to the field of physiological examination and/or analysis of tissue, especially in vivo examination of human tissue, and also to the general field of optical (light) propagation and response technology, and to the application thereof; more particularly, the invention relates to methodology and apparatus involving the combination of these two such fields. Still more particularly, and in some of its more specific attributes, the invention relates to certain novel applications and methodology in examination of, and the production and presentation of clinical physiological data with respect to, human female breast anatomy by use of optical response observations, involving response measurements and characterization, and including spectral response by way of transmissibility, reflection and scatter aspects and relationships.

BACKGROUND

In academia, and particularly in biological and medical research activities, amont practically innumerable studies, experiments and laboratory examinations, a relatively small but frequently recurring interest has been shown in the use of light, in various different forms, as an investigative and/or diagnostic tool or instrumentality. A relatively primitive emanation of this interest is evidenced in the various forms of transillumination which have been experimented with and used in many different ways over a great many years, probably dating back into antiquity, and in general utilizing light relatively crudely, i.e., as a visual aid, to help produce visually-perceptible shadows, shapes and images within or upon what would otherwise be substantially opaque objects or surfaces. In other more complex procedures, light energy of particularly selected parameters is impinged upon or injected into the subject matter to be investigated and interpreted from the standpoint of the quantity or nature of the light detectable at another location, typically opposite the point of injection. This approach frequently includes the use of spectrometers at the point of detection, and may or may not involve the use of particularly-selected wavelengths of light for application to the subject under study.

Thus, in earlier efforts utilizing basic transillumination, a typical approach would be to utilize a source of visible light coupled by a tubular shield or the like to a translucent body portion or object which is then viewed carefully from the opposite side with the human eye, often aided by various reflectors, magnifiers and the like. One immediately-available example of such a procedure is that utilized by physicians for examination of human sinus conditions. An example of the more complex type of procedure would be a scientific study such as for example is illustrated in scholarly publications of the type entitled "Infrared Microspectrum of Living Muscle Cells," by Darwin L. Wood (*Science*, Vol. 1, July 13, 1951), in which different particular individual types of muscle fibers were placed between transparent plates and placed in the radiation beam of a microspectrometer, where they were subjected to various wavelengths of light up to about ten microns, with the detected transmission intensities being plotted according to wavelength. With respect to the efforts to use transillumination generally, further reference is made to publications such as that by M. Cutler, M. D., in the June, 1929, issue of *Surgery, Gynecology and Obstetrics*, entitled "Transillumination As An Aid In The Diagnosis Of Breast Lesions," and as to the more complex spectrophotometric procedures, reference is made to an article in the Aug. 5, 1949, issue of *Science* (Vol. 110), by Blout and Mellors, entitled "Infrared Spectra Of Tissues."

While the aforementioned article by Cutler discussed basic transillumination procedures for diagnosis of breast disease as early as 1929, a number of proposals for refinement and enhancement of the basic transillumination procedures have been suggested in intervening years. Thus, the use of color film was proposed in 1972 by Gros and Hummel, and Ohlsson et al. proposed in 1980 the use of infrared film rather than ordinary color film, both using visible yellow light as well as infrared or rear infrared light as the illumination. Carlson has further proposed the use of a Vidicon system as a detector or collector, but the ultimate analysis and interpretation is nonetheless done visibly.

In the area of spectrophotometric analytic and diagnosis efforts, infrared oximeters have been developed and utilized in relatively recent years for non-invasive monitoring of the oxygenation of blood in humans and other specimens, most typically by contact with the ear or a finger extremity, a selected infrared wavelength being coupled to the involved body portion with detection occurring on the opposite side of such portion, variations in the light energy detected being directly indicative, after appropriate calibration, of the oxygen content of the blood flowing through the affected body portion, as a result of the known absorption references of particular infrared wavelengths by oxygenated hemoglobin. Somewhat analogous observations and/or phenomena may be discerned by contemplation of publications such as those by Blout and Mellors, noted above, which noted a dramatic increase in the intensity of light at the 9.3 micron band in cancerous breast tissue as compared to normal breast tissue and the proposed explanation that the 9.3 micron band is also one of the strong intensity bands for the enzyme ribonucleaes, which rapidly increases in amount in rapidly proliferating cancer cells. Various publications of Frans Jobsis commencing in about 1977 and including U.S. Pat. Nos. 4,223,680, 4,281,645, 4,321,930 and 4,380,240 are based upon a somewhat analogous although specifically different reported phenomena, i.e., the spectrally distinctive absorption characteristics associated with the cellular enzyme cytachrome a, $a_3$, which in turn is said to be integrally associated with, and indicative of, oxydative metabolism. On this basis, Jobsis proposed the use of a particularly-selected measuring wavelength and another carefully selected reference wavelength to produce apparent differences in detection level, which differences were said to demonstrate, and actually be indicative of, organ vitality or viability, since indicative of oxydative metabolism and therefore of oxygen sufficiency, the premise being that the chain of causation between the observed measurements and the body organ believed to be under investigation, i.e., internally subjected to the injected light, was complete and inclusive.

BRIEF SUMMARY OF THE PRESENT INVENTION

In a broad and underlying sense, the present invention rests upon a basic foundation of optical response characteristics, and physiologic conditions and principles, generally including those expressed above but being more extensive in scope and modality as well as more expository in interpretation, and involving the effects of light scatter and transmissibility within the tissue under observation. That is, from one standpoint, the invention is broadly based upon the principle that light, and especially selected wavelengths of light (generally within the band of from 0.6 micron to 1.5 micron, by way of example, depending on the thickness of the subject) is transmissible through at least portions of the human body in varying degrees and in varying ways involving significant variations in reflection and scatter effects.

Thus, it has been found in accordance with one aspect of the invention that a given body portion will, when suffused with a selected light source (and particularly a sequence of selected light wavelengths), exhibit a definitive and repeatable optical response, e.g. response characteristics, which may be used to provide a "signature" or profile which demonstrates physiological condition and composition and, it is believed, shows abnormalities or anomalies, particularly when compared to other readings, e.g., profiles, taken from the same individual (i.e., person) both at other points in time and/or from other and complementary or analogous body portions (e.g., the opposite breast), as well as when compared to readings or profiles, and/or composites thereof, taken from the same body portions of other humans, especially related groupings of particular humans.

Further, the invention provides methodology and apparatus for obtaining optical response data indicative of intrinsic tissue characteristics and independent of individual and ethnic factors such as color, degree of pigmentation, age, skin thickness, etc., which is uniquely useful in the above-noted type of approach, as well as in other and more general clinical ways.

More particularly, the invention provides methods and apparatus for obtaining spectral transmissibility data for clinical study and analysis, particularly of the human female breast, to provide a further clinical instrumentality for the study of the breast, hopefully to help bring about better understanding of its physiology, particularly with respect to the aging process, and also with respect to the occurrence and nature of anomaly, abnormality and hopefully of disease and/or other adverse conditions and states.

In a broad sense, the invention is directed to a new method and apparatus for obtaining optical response data profiles by examining biological tissue in vivo, and particularly the human female breast, yielding highly useful information as to the intrinsic composition, condition and physiology of an internal volume of tissue whose location and size depends upon the relative positioning and location of optical probes.

In a more particular sense, the invention contemplates the injection of light (and particularly, sequential bursts of selected light wavelengths, or narrow bands) into the breast (or other selected body part) at a given location and the detection of the amount of resulting light which emerges and is detected, or received, at at least two locations, one relatively nearer the point of injection and one or more others located relatively farther from the injection point. The two detection locations are chosen to satisfy two conditions; i.e., the injected light must have similarly passed into and out of the skin at each different location, and the light must have sampled (propagated through) different areas and amounts of internal tissue. By comparative analysis of the resulting light reception data, effects related to impingement and entry (as well as exiting) of the light through the skin are cancelled out, leaving only data which pertains to the internal tissue. Further, the geometrical locations and spacing of the light receivers is known and the nominal optical distance and particularly the difference between the optical distance between the location of the near receptor, or receiver, and that of the far receptor or receiver, is determined in accordance with the invention and used as a normalyzing factor in arriving at the light-reception data which is profiled. Thus, such data is appropriate for use in direct comparative studies of, and for averaging and compositing with respect to, different individuals regardless of whether they are of the same or different racial, ethnic or pigmentation characteristics, and regardless of particular physical differences and the like, from one subject to another.

BRIEF DESCRIPTION OF THE DRAWINGS

FIG. 2 is an enlarged, sectional side elevation of the direct-transmission receiver component member, in accordance with one embodiment of the invention;

FIG. 3 is a sectional, side elevation of the apparatus shown in FIG. 2, taken along the plane III—III thereof;

FIG. 4 is an end elevation of the apparatus shown in FIG. 3, as seen along the plane IV—IV thereof;

FIG. 5 is a sectional, end elevation taken along the plane V—V of FIG. 2;

FIG. 6 is an enlarged, sectional side elevation similar to FIG. 2 but showing the light-transmission and reflectance-receiver component member;

FIG. 7 is a sectional, side elevation taken through the plane VII—VII of FIG. 6;

FIG. 8 is an end elevational view of the structure seen in FIG. 7;

FIG. 9 is a sectional, end elevation taken along the plane IX—IX of FIG. 6;

FIGS. 14a, b and c are a three-part graphical representation showing preferred ways of visually presenting spectrophotometric physiological data in accordance with the present invention.

DETAILED DESCRIPTION

Figure 1:
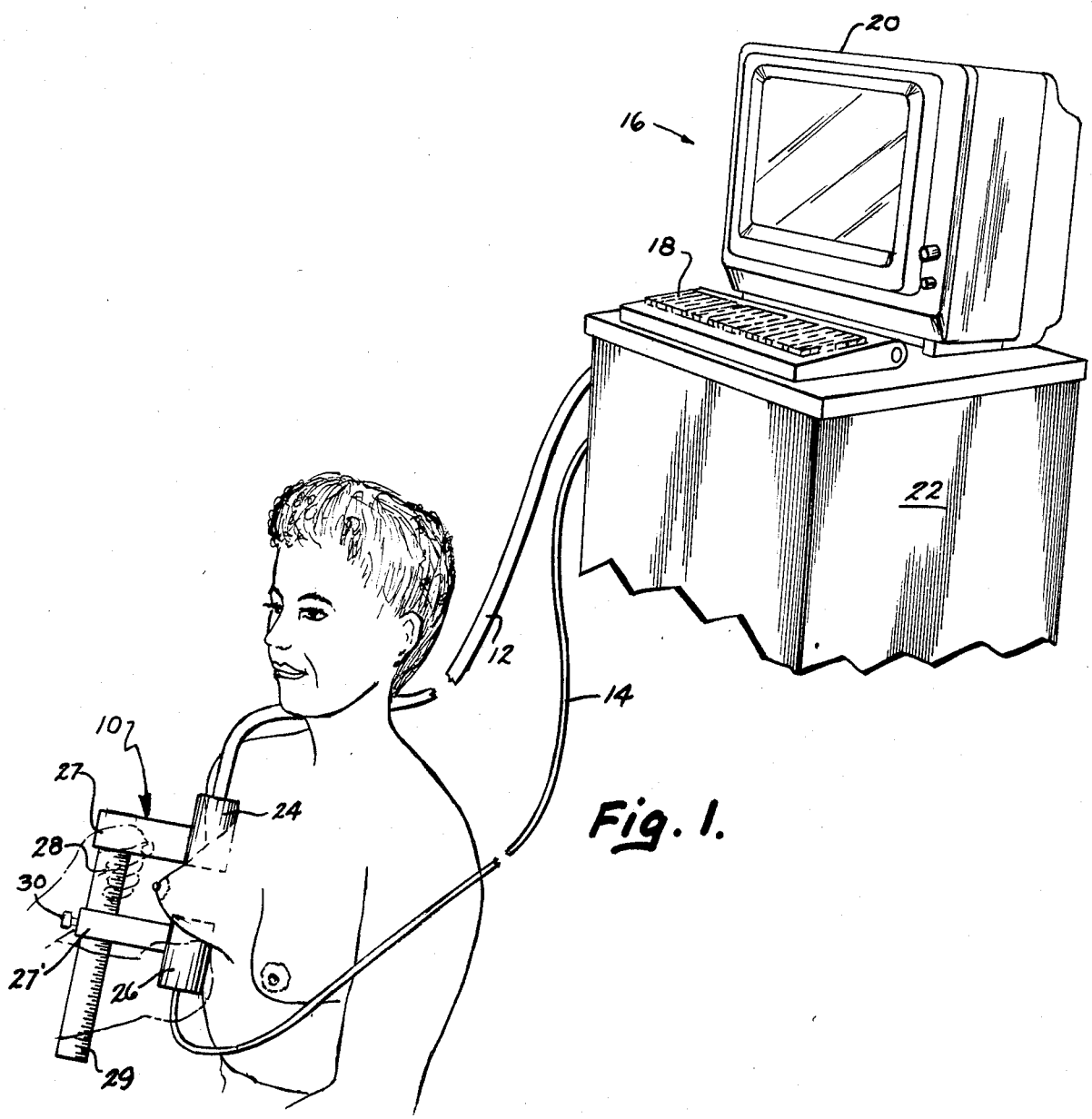
FIG. 1 is a pictorial perspective view showing apparatus in accordance with one embodiment of the invention and depicting its general manner of use.

The general nature and general usage of one form of apparatus in accordance with the invention is illustrated pictorially in FIG. 1. Stated in the most basic terms, optical measurements or readings are taken by use of a manually-manipulatable test instrument 10 which is coupled by cables 12 and 14 to a control unit 16 which includes an input keyboard 18 for actuation and control purposes, a CRT visual display 20 on which data may be displayed in various formats, and a housing 22 in the form of a cabinet which encloses associated light sources, electrical supply apparatus, data-handling electronics and data-processing apparatus including for example a microcomputer (which may be a small digital device of the type known as a "personal computer", e.g, the IBM "P.C." or generally similar device), together with interconnected data storage (e.g., floppy disk drive) and a digital plotter of a conventional nature.

With continuing reference to FIG. 1, it will be observed that the test instrument 10 includes a first side or portion 24, referred to hereinafter as a "component member," as well as a second such portion or component member 26, both of which are disposed in mutually-aligned opposition in this embodiment of the apparatus, and the mutual alignment (geometry) selected for the particular application is maintained by support means comprising, in this example, fixed and movable carriers 27, 27', respectively, mounted upon a rigid interconnecting alignment and positioning bar 28 which carries length-measurement indicia 29. The movable carrier 27', to which component member 26 is attached, is slidable along the positioning bar 28, and a thumb screw or like securement means 30 is provided for fixing this carrier, and thus the component member 26 associated therewith, at a desired point of adjustment along the slide bar, at which the component members 24 and 26 have been positioned in the desired relationship relative to the subject, or patient. In this respect, it is to be understood that the slidable carrier 27' is maintained in a given desired geometric relationship (in this example, parallelism) with carrier 27, which may be fixed to the end of positioning bar 28, indexed at the "zero" position of the indicia 29, such that at any desired position along the length of the bar 28, the two component members 24 and 26 will be in consistent mutual alignment with one another (here involving certain axial relationships more particularly described hereinafter) and that such positioning will be retained upon tightening of the thumb screw or securement means 30.

While many different particular structures or mechanisms might well be utilized for the basic purpose of maintaining a given desired geometric relationship, i.e., "alignment", of the two component members while permitting any desired relative movement, one relative basic arrangement for axial relationships is that of a modified dial caliper, having the cross section of bar 28 in the form of a rectangle, and providing a complementary rectangular recess through movable carrier 27', such that the complementary shapes permit relative sliding yet maintain the desired alignment. In such an arrangement, a simple threaded thumb screw passing through a threaded aperture in the bottom portion of movable carrier 27' and aligned to bear against the adjacent edge of the bar 28 will serve as an entirely satisfactory indexing means, permitting the distance between the two carriers 27, 27' (and thus between the two component members 24, 26) to be fixed and easily read visually.

The significance of the nominal optical distance information read from the indicia on the bar 28 will be explained more fully hereinafter, but it should be noted that the availability and utilization of this information is decidedly important to the invention. Thus, whatever spacial relationship or geometry is desired in a given embodiment, the support, means utilized must be arranged to provide the effective or nominal optical distance, whether the component members are fixed or movable. In the embodiment just described, this information is entered into the computer via the keyboard 18 by the operator, but it may be preferred to utilize a form of the test instrument 10 having a transducer which automatically inputs this information as a coordinated part of the overall procedure.

As may further be seen in FIG. 1, the test instrument 10 is utilized to place the two component members 24 and 26 on opposite sides of the breast or other such body extremity which is to be examined pursuant to the present invention. In the case of the human female breast, several different readings are preferably taken, for purposes discussed more fully hereinafter, at four positions: centrally of the breast and near the chest wall; on the inside edge or marginal extremity of the breast (i.e., on the side nearer the center of the chest); along the outer marginal edge of the breast and generally across from the inside measurement just noted (both such measurements preferably being accomplished at a relative position somewhat further out from the chest wall than the first reading noted); and at a location which is generally centrally of the breast but as far outward from the chest wall as practicable, behind the nipple. In this respect, depending upon the particular anatomy of a given patient, certain such readings may at least slightly overlap, although in other cases they will not. The orientation of the test instrument, and of the two component members, is preferably generally vertical in these different measurements or readings due to the interstructure of the breast, which is much more symmetrical from one vertical section to the next. Thus, the instrument is moved from place to place by manual manipulation, in each instance the two component members being moved apart to the extent necessary, placed over the breast in the desired positioning, and then gently moved toward one another to the extend necessary to provide full contact between the inner surface of each component member and the breast, so as to preclude the entry or exit of any light from between the breast and each of the component members.

The component member 24 is seen in more detail in FIGS. 6, 7, 8 and 9. As seen there, the structure of this member includes a cylindrical outer shell or cover 32 which is closed at one end (the rear, as referred to herein) by a circular connector deck 34, and which at its other end has a forwardly projecting cylindrical nosecone 36 whose central opening may be covered by an optical filter 38, an element primarily useful for environments having ambient lighting which would interfere with the optical responses to be obtained. For example, under such conditions a "safe light" may be used in combination with a complementary filter; e.g., a blue-green safe light where infrared light is most important, complemented by an orange filter as element 38. The outer shell or cover 32 may be a thin metal member, and the connector deck 34 may also be of metal, preferably brass or aluminum, to provide for optimum electrical grounding. The nosecone should be of a material which is opaque to infrared light energy, such as for example a filled epoxy, and the nosecone and outer shell should telescope snugly together and may be slightly tapered to enhance a close-fitting relationship. Inside the outer shell 32 and the nosecone 36 is a generally flat support plate 40 which bottoms against the connector deck 34 on one end and directly contacts a circular detector deck 42, to which it is secured in a desired manner, as by adhesive or screws, and the peripheral edge of the detector deck seats in and against the edges of an annular shoulder formed in the inside of the nosecone. The support plate 40 is likewise secured at its opposite end to the connector deck 34, which has a peripheral shoulder which snugly receives and seats the end of the outer cover 32, such that the entire assembly is a rigid unit, around which an annular upper portion of the carrier 27 fits, and is secured.

Inside the component member 24 is the forward end extremity of an optical fiber cable or bundle 44, which enters through an appropriate aperture in the connector deck 34 and which projects forwardly, generally parallel to the support plate 40 (to which it may be secured by an appropriate clamp [not shown]), beyond which it passes through both the detector deck 42 and the filter plate 38, preferably terminating om a stainless steel or like ferrule 46. Also, within the component member 24, is a pair of optical detectors 48 and 50, which seat within appropriate apertures in the detector deck as well as in appropriate grooved or recessed portions in the end of the support plate 40. The detectors have electrical leads or conductors 52 which exit the component member through the connector deck 34, preferably through an appropriate connector 53. At the forward end of the component member, a thin plate-like septum 54 is fixed into position between the forward surface of the detector deck 42 and the rearward surface of the filter 38 to provide optical isolation of the detectors 48, 50 from the optical fiber bundle 40, and this effect is furthered by providing an arcuate reception slot 56 extending through the filter plate 38, through which light energy must pass in order to be received by either of the detectors 48 and 50. Arcuate slot 56 is in fact a segment of a circle which is centered upon the optical fiber 44 and the distance (radius) between the optical fiber cable and the reception slot should, in the embodiment under discussion, be in the range of about one to three centimeters, preferably not more than about two centimeters. This distance is important, since in this embodiment the detectors 48 and 50 are "near" detectors whichare intended to receive directly-returned þreflected" light energy, i.e., light which has been introduced ("injected") by the optical fiber bundle 44 into the particular body portion or extremity with respect to which clinical data is desired to be obtained, and which has in fact entered that body portion and has encountered initial reflection and "backscatter" from the internal tissue directly beneath the skin.

Thus, the "reflected" light energy detected by "near" detectors 48 and 50 has passed through the skin of the subject to enter the internal tissue of the breast (or other body portion) but has immediately exited by passing back outward through the skin toward the source. This "near" detection signal is very important in accordance with the invention, as will be explained more fully hereinafter, and should not include light which has merely passed directly from the end of the fiber optic, over the end extremity of the septum 54, and directly into the detectors 48 and 50 without ever having passed into and out of the skin of the subject. Also, in this embodiment, the detected light energy should represent light reflected immediately back at the source, which has not traversed substantial distances within the breast tissue itself and emerged far away from the source; consequently, the reception slot 56 and the detectors 48 and 50 themselves should not be located more than the indicated distance from the point of light injection.

The "direct transmission" (i.e. the "far") detector component 26 for the embodiment under discussion is illustrated in FIGS. 2, 3, 4 and 5. This member is substantially the same in basic structure as component 24 discussed above, including an outer shell 32', a circular connector deck 34' at the rear through which an electrical cable 14 enters and exits the component member, preferably via an appropriate connector 53'. Within component 26 is a support plate 40' and a detector deck 42', all secured together generally in the manner discussed above with respect to component 24. In the case of this "far" component member, however, four detectors are preferably present, i.e., detectors 58, 60, 62 and 64, all mounted generally in the manner referred to above with respect to detectors 48 and 50, i.e., protruding through the detector deck 42' and disposed within appropriate recesses in the forward end of the support plate 40'. As in the case of component member 24, component member 26 also includes a septum, designated 54', but in this case the septum separates and helps to optically isolate pairs of detectors, as best illustrated in FIG. 5, detectors 58 and 64 being in one such pair and detectors 60 and 62 being in the other such pair. In the case of component member 26, a filter plate such as that previously described (and designated by the numeral 38) may also be used if necessary, depending upon circumstances involved in the test environment, but is not included in FIGS. 2, 3 and 5.

It should be understood that terms used herein such as "direct" or "transmitted" and "reflected" or "scatter" are adopted primarily for purposes of convenience and illustration, and not to indicate that there are fundamental differences between the light energy that emerges at any given point from the selected body portion after injection. Actually, it is believed that all injected light undergoes multiple and diverse scatter effects throughout its tortuous path of propagation within the breast or other body portion in which it has been injected. Thus, the present invention contemplates use of the overall optical response provided by comparitive analysis of the "near" and "far" detection signals, which response is viewed as complex in nature and quite conceivably involving molecular (Rayleigh) scattering, particle (Mie) scattering, index (Fresnel and Christiansen Effect) scattering, fluorescence (especially infrared fluorescense), inelastic (Raman) scattering, and both spectral and non-spectral energy absorption. Thus, the circumstances and the methodology are considerably more complex than simple in vitro laboratory spectrophotometry, and the responses profiled in accordance herewith may well depend upon such factors as molecular structure, the types and size distributors of cells, the amount, nature and distribution of fat cells and of connective tissue, the blood supply and vascularization metabolism, the lymph system, and glandular activity.

Figure 10:
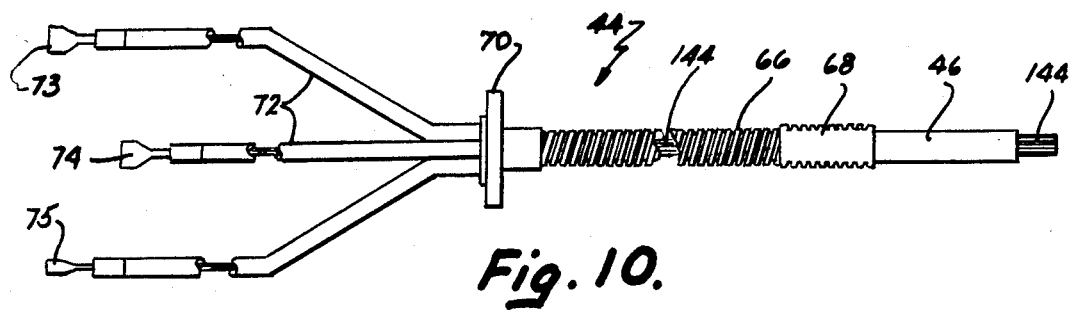
FIG. 10 is a fragmentary, plan view, on a reduced scale, showing one embodiment of a fiberoptic cable assembly for use in interconnecting portions of the apparatus.

The optical fiber cable 44 referred to above in conjunction with FIGS. 6, 7, 8 and 9 is seen in somewhat more detail in FIG. 10, which illustrates that the aforementioned ferrule 46 terminates a brief distance inward from the actual end of the bundle of optical fibers 144, corresponding to the thickness of the filter plate 38. The main bundle 144 of optical fibers is preferably sheathed, as for example by a flexible helical conduit 66 extending over that portion outwardly of the cabinet 22 (FIG. 1) and an external sleeve 68 of plastic or the like may be utilized for stress relief. A mounting flange 70 is shown to illustrate a preferred structural attachment of the optical cable to the cabinet 22, and the portion of the cable which is to be disposed within the cabinet may simply be covered by protective cladding or lightweight tubing 72. As illustrated (FIG. 10) this latter portion may be divided into more than one branch (three being illustrated) in the event multiple light sources are to be uitilized, each branch terminating in appropriate light-coupling optical terminals 73, 74 and 75, which may be physically sized differently from one another in a manner best suited to optically match the particular source to be coupled thereto.

As indicated previously in conjunction with the discussion of FIG. 1, the component members 24 and 26 are in the particular embodiment under discussion, held in direct alignment with one another by the carriers 27, 27' and the bar 28. More particularly, in this embodiment the alignment is such that the light-injecting fiber optic 44 is substantially aligned along the same axis with one pair of the "far" detectors, e.g., detectors 58 and 60, the other such pair of detectors thus being disposed a predetermined distance off-axis. This is for purposes of comparison and data-enhancement, as pointed out more fully below.

In accordance with a particular aspect of the invention, one or more different light sources may be utilized to provide a relatively large number (on the order of about twenty) of different wavelength spectra (spectral groupings) within the total spectrum of about 0.5 microns to perhaps 2.2 microns, and particularly within the range of about 0.6 to 1.5 microns, the wavelength resolution preferably being on the order of about 15 nanometers (nm) in the visible range and about 30 nm in the infrared range, which spectral array is conducted through the optical fiber cable 44 to the component member 24, from which the different light spectra are sequentially injected into the body portion under examination, e.g., a breast. That is, each such source scans or steps through its particular different wavelength groupings one after another, with a relatively brief "dwell" for each particular different grouping. Accordingly, the various detectors will produce outputs in a corresponding sequence, each particular such output thus being correlated to and representing a measure of the intensity of the light energy received at a particular detector location as a result of a particular narrow wavelength grouping of light injected or admitted. With respect to particular examples of light sources, use of scanning monochromators and an interference filter wheel are contemplated, for example in an arrangement where each provides a portion of the overall desired wavelength spectrum. An OCLI variable filter wheel may be the most preferably monochromator, at least for the "visible" light portion of the spectrum desired (and possibly for certain of the "near" infrared spectra) because of optical efficiencies provided which will increase the amount of light injected. The light sources themselves should be "chopped", as by an optical shutter (rotating apertured disc), to reduce low-frequency background and "common mode" noise, and the detectors should thus be switched synchronously with the chopping of the sources.

Somewhat more particularly, with respect to the particular source of illumination, a tungsten filament quartz-halogen lamp may be utilized, with imaging of the filament onto the entrance apertures of the monochromators, with optical power input to the body portion under examination running from aout 1.4 milliwatt at the lower end of the spectrum to about 1.9 milliwatt through the visible portion of the spectrum and perhaps on the order of about 3 to $3\frac{1}{2}$ milliwatts over the infrared portion of the spectrum (depending upon the thickness of the body portion being scanned). The optical filter selected for use should desirably augment the source over the infrared portion of the spectrum, with particular filters being cut to the various water windows and water absorption bands involved. That is, as illustrated in FIG. 11, it is known that contrary to what a lay person might expect, ordinary water has the property of varying transmissibility to light, having several very pronouned "absorption bands," i.e., strong light-absorption characteristics, at particular wavelength bands, separated by "windows" in which the transmissibility increases markedly between the preceding absorption band and the next succeeding one.

Figure 11:
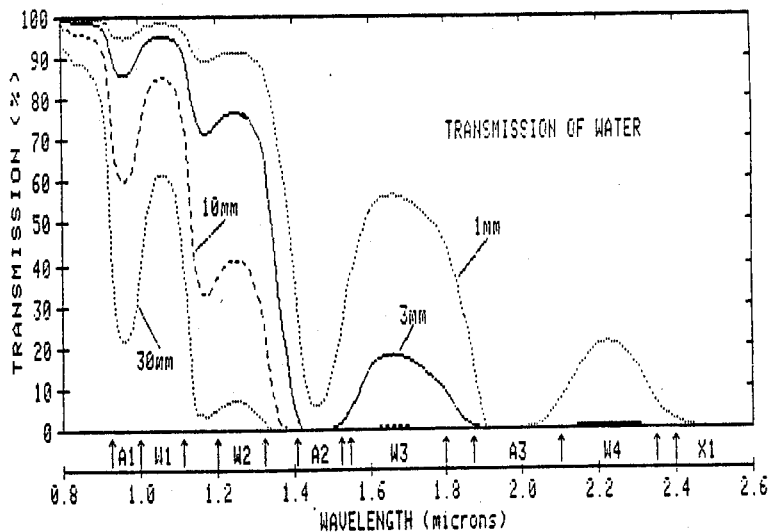
FIG. 11 is a graphical representation showing light-transmissibility characteristics of water.

Referring more particularly to FIG. 11, considering the transmissibility of water for varying distances at wavelengths from 0.8 microns to about 2.5 microns, at distances ranging from 1 millimeter (top curve), 3 millimeters (second from top curve), 10 millimeters (second curve from bottom) and 30 millimeters (lowermost curve), strong absorption bands will be seen to exist over areas designated A1, A2 and A3, occurring at approximately 0.9–1.0 microns, 1.4–1.5 microns, and 1.9–2.1 microns. Between these absorption bands, strong transmissibility "windows" may be seen at approximately 1.0–1.3 microns, 1.7–1.8 microns, and at about 2.2 microns. The absorption bands and transmissibility windows will thus be seen to produce striking results, since at transmission distances of 1 millimeter and 3 millimeters, light is substantially fully absorbed at wavelengths of approximately 1.5 microns and approximately 2.0 microns, but a very strong (by comparison) transmissibility band exists between these wavelengths.

These characteristics have more than casual significance to methodology such as is contemplated herein, since human body is of course comprised of a preponderance of water, and transmissibility characteristics of human tissue must therefore be anticipated as exhibiting somewhat similar characteristics, or in any event as encompassing the same technological phenomenon. In this respect however, it should be noted that different types of tissue embody different water content; for example fatty tissue has much less water and it is less tightly bound by the molecules; thus, fat tissue exhibits much greater optical transmissibility per unit thickness than does glandular tissue, for example. That is, the type of water binding involved in the tissue of a particular body portion will significantly affect the optical response, particularly transmissibility, since tightly-bound water has a much different response than weakly-bound or free water. An example of water content affect on a more general basis may be seen in FIG. 12, in which the transmissibility of fused quartz of one meter length is illustrated for two different gradations or degrees of quartz purity, namely, two parts per thousand water (left-most curve) and three parts per million water (right curve). In view of this, it should be understood that the fiber optic bundle used in accordance herewith should be of the latter type, i.e., having very minimal water content. FIG. 13 is further illustrative of conditions to be encountered, showing the general characteristics of, and marked differences between, the response of oxygenated hemoglobin on the one hand and reduced (oxygen depleted) hemoglobin on the other hand within the range of 600 nm to 850 nm, actual crossover of the response curves being present.

Figure 12:
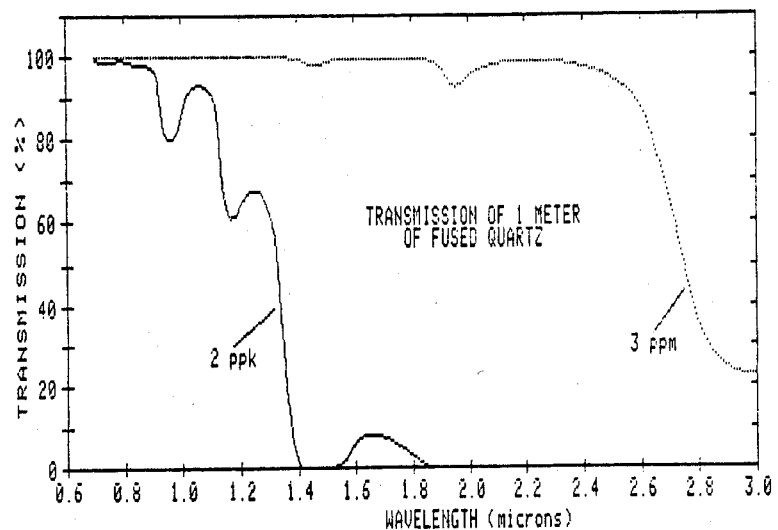
FIG. 12 is a graphical representation showing light-transmissibility characteristics of fused quartz.
Figure 13:
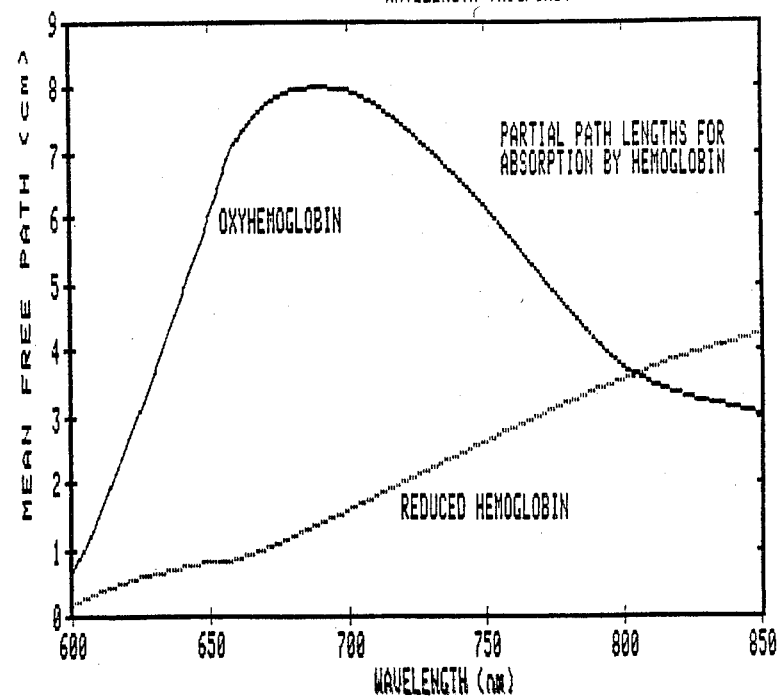
FIG. 13 is a graphical representation showing light-transmissibility characteristics of hemoglobin.

As may well be perceived by contemplation of FIGS. 11, 12 and 13, attempted optical (light transmission) examination procedures in living tissue will inevitably be highly affected, even to the extent of obscuring meaningful results, if accountability of water absorption and oxyhemoglobin characteristics is not fully considered. In particular, the water absorption windows must be taken into account, preferably by eliminating the effects from the test instrumentality itself (i.e., choosing optical fibers having the least adverse response), and by the aforementioned approach of selecting the optical filters on the basis of the water absorption bands and transmissibility windows. A further and analogous consideration is the noted absorption characteristics of oxygenated and reduced hemoglobin, which is of course present in great abundance in living human tissue and which should thus be similarly taken into account, either by avoidance or by appropriate compensation in the analysis of the resulting data.

To a substantial degree, a primary aim of the present invention is to obtain clinical, physiological data for selected body portions, and particularly of the female breast, by optical response methodology, and in a more particular sense, to obtain such clinical data on the basis of intrinsic, internal tissue properties; that is to say, to produce data which will be applicable from one individual to another, for widely-based comparison and classification. This requires that the data be free of the effects of individual particularities such as for example, skin differences, including pigmentation, color, thickness, etc., as well as breast thickness, and other particular physical characteristics. Such an achievement is of fundamental importance in pursuit of the particular type of methodology involved here (i.e., optical response analysis or study of living subjects, and in particular of living human subjects), since without these essential refinements, there can be no truly meaningful correlation between any two different individuals having a normal range of individual differences.

In accomplishing the aforementioned objective, the above-disclosed method and apparatus for readily determining (reading out, or establishing in advance) the particular distance between the component members of the optical probe (i.e., the "nominal optical distance") involved in a given measurement or scan is of surpassing importance, as is the determination and appropriate usage of both "direct" light transmission or propagation data (i.e., "far" data) as well as "reflective" (i.e., "near") data. With respect to the second such point, a significant feature of the present invention is the realization that "reflected" (i.e. "near") transmissibility data should be obtained and in effect used as a measure of the light energy actually injected into the interior of the body portion under examination, after the effects of impingement upon and passage through the skin, etc. From this "near" detection level is substracted the "far" or "direct-transmission" data, since by so doing one may compare the amount of light energy which has passed completely through, or at least traversed a substantial portion of, the breast or other body portion to the amount of light energy actually injected into the internal tissue initially, and thus remove from consideration all of the many data-modifying characteristics arising from individual differences of skin. This in effect provides data which is truly a gauge of intrinsic, internal tissue characteristics, which may be accurately correlated with similar data taken from other different body locations and/or other individuals.

Furthermore, the knowledge and appropriate utilization of the particular nominal optical distance involved in each different optical scan over whatever different wavelength spectra have been selected and over whatever different body portion or path has been selected is similarly of great significance, since this optical distance is utilized in accordance with the invention to in effect further normalize or condition the data obtained and thus remove the otherwise inherent variation of light energy propagation as a function of optical distance or thickness. In this connection, it should be clearly understood that the particular arrangement illustrated, with axial alignment of the receivers and close positioning of the "near" detector to the light source, is not at all the only effective such arrangement. That is, while at least one "near" and one "far" detector are required, they need not be positioned on a straight-line basis if some other (e.g. relative angular positioning with respect to the light source) arrangement is desired, as for example to better accommodate a particular anatomical area to be studied. In any such arrangement, the effective or nominal optical paths involved for the particular positions of the receivers must be determined, and the difference between such optical distances determined, since that difference (representing the different tissue volume sampled by the far receiver) is the essence of what is intended by use of the term "optical distance" herein. That is, in the particular example illustrated the close proximity of the near detector to the point of light injection may either be assumed to represent a zero optical distance for that detector or else the very short actual distance for it may be "built into" the scale which is read to determine the optical distance for the "far" detector. In any case, utilization of the measured or otherwise-determined effective or resultant optical distance is accomplished both by using it to compensate for inverse square reduction of propagated light intensity and also as the "thickness" parameter in application of the exponential function attributed to Beers and known as Beers' Law, to develop intrinsic light propagation magnitude values for the internal tissue of the selected body portion.

While it is not the purpose of this disclosure to focus upon any particular methodology and/or apparatus for actually making this data compensation or specifically implementing the data-conditioning principles, it may be noted that data-handling procedures of this general nature are readily and indeed routinely obtained through use of known techniques and routines in the use of digital computers, and that appropriate results may also be obtained directly through electrical signal-processing approaches, in hardware (circuitry), since discrete digital components such as adders, subtracters and digital dividers are of course in widespread use and widely diverse availability. It is the general underlying principle and methodology of such approaches which is here involved, i.e., arrival at intrinsic-type data by conditioning the signal values actually received from the "far" receivers in the "direct transmission" mode through use of the "near" receiver "reflectance transmission" data, together with use of the nominal optical distance measurement determined for each particular measurement set.

Further aspects of the methodology involved in the present case are the aforementioned concepts of taking multiple different data scans at different predetermined positions on the same body portion (in particular, the human breast), as well as on comparable or complementary body portions on the same person (e.g. the opposite breast) and by use of similar scans taken at like positions on like portions of other persons (and including averaged or composite such scans, classified as by age or condition for example), all obtained by use of the same or substantially the same spectral transmissibility procedures, involving numerous different wavelengths of light with resulting multiple data points on a wavelength-specific basis, with subsequent presentation of the resulting data in the form of graphical or tabular profiles for study and consideration in documenting the characteristics of a given person at a given point in that person's life, together with analysis for determination of individual characteristics and anomalies present at the time of the particular scan or set of readings.

In this respect, the resulting data, to be commented upon more specifically herebelow, may advantageously be displayed both by tables of magnitudes and by plotting the compensated and weighted magnitudes with respect to wavelength, not only by means of separate graphical presentations for each different location from which data is obtained, but also by taking complementary scans of complementary body portions, i.e., in the case of breast examinations, by taking a set of measurements for both breasts with similar relative positioning of the hand instrument 10, i.e., both left and right breasts along the inner (central) marginal edges, along the outer marginal edges, centrally near the chest wall, and centrally outward away from the chest wall. The resulting data provided in accordance with the invention may also be presented in the form of color maps, by use of known color-mapping programs commercially available for digital computers of the type referred to herein. For example, the data obtained for particular wavelength groupings may be assigned different colors, and the colors overprinted within a map area as a function of received signal intensity after conditioning as described hereinabove. This will yield yet another form of data presentation which will have widely-differing color content and distribution, according to the characteristics of the tissue sampled, which will have different evaluative effects for different persons which may be preferred by some. Regardless of which particular form of data presentation is selected, the formatted data may then be meaningfully compared to similarly formatted data for the same patient, and the records so obtained preserved for comparison with similar records taken at other points in time. Further, such results may be comparitively examined with respect to other results obtained from other particular individuals, both those who may be known to be "normal" (i.e., not known at that time to possess specific and identified abnormality or disease), as well as for those who may have diagnosed abnormality or illness.

A further point in the foregoing connection involving the particular methodology and apparatus disclosed herein, relates to the use of duplicative or dual reception means at the different locations in the component members 24 and 26, as already mentioned generally hereinabove. That is, considering the total spectrum of the various wavelengths which may be utilized in accordance with the invention, as noted above, it has been determined that each of the "sets" or "pairs" of detectors at both the far transmission receiver, or component member, 26 and also at the near receiver or component member 24 are preferably comprised of two different types of detector elements, one of which is more effective over the shorter wavelength portion of the spectrum and the other of which is more effective over the longer wavelength portion, with an area of commonality or overlap in the midrange. For example, silicon photovoltaic cells are desirable for receiving the chopped "visible" light wavelengths of from about 0.5 to about 1.2 microns, while lead sulfide (PbS) photoconductive cells provide some advantages in the higher, infrared wave length ranges, actually providing useful results throughout the range of from about 0.85 to about 2.2 microns, even though involving substantially higher noise production than the silicon photovoltaic cells. A possible alternative to the lead sulfide cells (detectors), may be a zero-bias germanium photovoltaic cell, whose band gap is essentially midway between silicon and lead sulfide, and which may be cooled to lower the effective noise equivalent power. Such germanium detectors would not provide detection to the longer wavelengths over which lead sulfide is operative, but does have the advantage of having a peak response in the neighborhood of about 1.5 microns, which may be at or near the only water transmissibility "window" beyond the 1.3 micron point. An alternative for the silicon photovoltaic cells is the silicon photodiode, having somewhat similar performance as the silicon photovoltaic cells, although they are presently deemed more preferred.

The dual-detector configuration just noted not only serves to produce useful data over a greater wavelength spectrum, but also has the added feature of providing redundant data over a shared midrange. To be sure, the absolute magnitudes of signals produced by the dissimilar types of detectors will be significantly different, but this of course may readily be balanced or compensated for by appropriate level-setting or gain-control procedures; consequently, the duplicative or redundant data produced over a certain portion of the transmitted wavelength spectrum, received at essentially the same position with respect to the light emitter or injector, is considered to be highly useful, since the data may be mutually compared to detect error sources, etc., and it may also be averaged together in order to increase accuracy and reliability. This same goal is served by providing the four-detector set in the "far" or "direct transmission" receiver or component member 26; that is, the "on-axis" set of detectors (comprising two different types of detectors, as discussed above) samples data from a conceptually different point (i.e., coaxially with the fiber optic) than does the adjacent set of "off axis" detectors (which also comprise two different types of detectors). The data obtained from these two conceptually differing detection locations may also be compared and averaged or combined in the general manner discussed above with respect to the two different types of detectors, at each different detected wavelength, i.e., each different narrow wavelength band comprising a step or unit of the light injected into the body portion under examination by the fiberoptic cable. Other techniques which take further advantage of the dual-dissimilar detector configuration are for example, a sequence of blocking first one and then the other with optical filters at selected points in the wavelength transmission spectrum, to provide greater flexibility and certainty for data-comparison and evaluation techniques. Where more than one specific light source is utilized, as for example two different monochromators, such blocking and filtering techniques may be utilized to insure transmission channel separation. It should be further noted that the silicon photovoltaic cells preferred for detection at the lower portion of the spectrum require a lower "chopping" frequency of the light source than do the lead sulfide photoconductive cells, due to the higher capacity of the silicon cells. For example, a useful frequency for use with the silicon cells is on the order of 13 Hz, whereas an optimum chopping frequency for the lead sulfide cells is on the order of about 220 Hz.

As will be understood, the output provided by each individual detector will comprise a series of magnitude or intensity readings measuring the amount of light energy received at that detector at the various points in time corresponding to the wavelength spectra produced by the light sources and injected into the body portion under examination. This analog-form electrical signal is conducted by the particular electrical lead or conductor within the electrical cable 14 which is associated with the particular detector involved. In this connection, it is to be noted that the component members 24 and 26 are, in the form illustrated, particularly sized to accommodate preamplifier circuitry, and additional processing circuitry if desired, within the enclosure or space 65 behind the detector element itself and alongside the support plate 40 in each component member. The resulting electrical signal, which is at least initially of analog form, is coupled by the electrical cable 14 back to the control cabinet 22 noted previously, which includes signal-processing and computing electronics, as well as the display apparatus already noted hereinabove. Alternatively, it should be noted, the light detection may be accomplished through use of fiber optic receivers, with the received light energy conducted back through such fiber optic to the detection circuitry, where the detectors would then be located.

Preferred signal-processing circuitry for the detector signals should include dedicated channels for each detector output, preferably of a type treating the detectors as current sources and including as entry-level components low-noise operational amplifiers such as the AD515H, to whose inverting input the detector output should be applied. This amplifier configuration will appear as a very low-impedance load to the detectors (essentially, a short circuit), and thus, with the operational amplifier connected in a current-feedback mode, virtually all of the signal strength will be shunted through the feedback resistor, such that the current output for the detectors will be linearly related to the input optical power. After such amplification, the detector outputs (which will, of course, reflect the chopping applied to the illumination sources) is preferably compressed by applying it to a logarithmic-function analog IC, following which it is converted to digital form by use of an A/D converter operated in a sampling mode at twice the chopping frequency and synchronized with the light source choppers. The logarithmic conversion before digitization, although not strictly essential, serves to expand the dynamic range of the data obtained from the detectors. Reconversion to linear form may be accomplished by use of a digital antilog IC, and the resulting data stream should be put through a subtraction stage in order to remove common mode (background) signal, after which the data should be averaged over a number of chopping cycles equal to one percent of the wavelength scan time. Thus, the final data for any given detector will consist of strings of repetitive bursts, each representing averaged detection signals from which background signal has been subtracted.

A desirable addition, or alteration, of the signal-processing electronics described above is to demodulate the chopped signal and integrate the result over a number of the chopping cycles before the initial logarithmic conversion. In the case of the lead sulfide detectors, it may be advisable to omit the logarithmic compression step, and go directly to the A/D conversion, due to the presence of substantial noise and the limited extent to which the total dynamic range they provide may be utilized, due to water absorption characteristics in living human tissue, particularly in actual in vivo examination of human anatomical portions. This is particularly true with respect to the female breast, which undergoes almost constant physiologic change both on a day-to-day monthly basis and, to a much greater extent, over a lifetime, there being great differences in the relative amount of water present from time to time, as well as in its form, which may be free or "bound," e.g., in protein molecules.

An example of typical (if somewhat simplified) data to be obtained from actual clinical measurements done in accordance with the present invention is depicted in Table I immediately below, which should be understood as showing relative magnitudes of detector data obtained at four different examining positions, as identified, on both the right and the left breast of a human subject. In this instance, the data in rows 2 and 6 was obtained near the chest wall at essentially the midportion of the breast, and the data in rows 4 and 8 was obtained at generally symmetrical upper and outer quadrant portions, rather than at the central and outer position identified above as now preferred for a fourth data-taking position. Also, instead of obtaining individual data readings at many different wavelengths, the numerical data presented may be taken as indicative of the maximum reading obtained by use of a single wavelength grouping or band under the indicated conditions, such maximal data (which is also representative of composite or weighted averaged data) having very evident significance even though being generalized or simplified when compared to the numerous individual readings at different wavelengths which the complete data scan described above would include. In either event, expressions such as "selected light wavelengths" are used generally in accordance herewith to designate any such procedure, regardless of how many wavelengths may actually be selected in a given application, and not merely to identify a procedure using all or a major portion of the particular wavelengths identified as making up the total useful spectrum for the methodology involved.

TABLE I

EXEMPLARY DATA FROM CLINICAL MEASUREMENTS

| | | "Direct" (i.e. Far) Transmission Data | "Reflection" (i.e. Near) Data | Direct/ Reflection (percent) | Average (percent) |
|---|---|---|---|---|---|
| RIGHT | | | | | |
| 1 | Outer Portion (outer third) | 386 | 3850 | 10.03 | |
| 2 | Mid-Portion (middle) | 147 | 4564 | 3.22 | 8.89 |
| 3 | Inner Portion (inner third) | 514 | 3834 | 13.41 | |
| 4 | Other | 299 | 2015 | 14.84 | |
| LEFT | | | | | |
| 5 | Outer Portion | 1206 | 2571 | 46.91 | |

TABLE I-continued

| | | EXEMPLARY DATA FROM CLINICAL MEASUREMENTS | | | |
|---|---|---|---|---|---|
| | | "Direct" (i.e. Far) Transmission Data | "Reflection" (i.e. Near) Data | Direct/ Reflection (percent) | Average (percent) |
| 6 | (outer third) Mid-Portion (middle) | 680 | 1976 | 34.41 | 43.04 |
| 7 | Inner Portion (inner third) | 1431 | 2993 | 47.81 | |
| 8 | Other | 975 | 3157 | 30.88 | |

Consideration of the data in the above Table will readily reveal the significance of the readings as a general indicator of condition. Thus, in comparing the readings in rows 1 and 5, for example, for the outer third of the right breast in comparison to the left breast, the differences in numerical magnitude shown reveal graphic differences in the underlying physiological conditions. Further significance can be drawn by comparing in a relative manner the "direct" (or "far") transmission data and the "reflection" (or "near") transmission data at each given sampling station, and for the same station on opposite breasts. The actual numerical ratio of "direct" transmission data to "reflection" transmission data is indicated in the third column of figures, and differences here are readily apparent upon casual examination; the same is certainly true with respect to the figures in the fourth column, which are the overall percentile averages of data for rows 1, 2 and 3 and 5, 6 and 7, respectively. In fact, this data is actually representative of measurements (data) obtained under clinical conditions from a living person ultimately diagnosed by other and conventional methodology to have carcinoma of the right breast.

FIG. 14 illustrates another useful approach in presenting data obtained in accordance with the invention, providing a series of graphical "profiles" for each patient or individual on the basis of paired curves for each different position of the examination instrument, the two curves in each pair representing the data for the two breasts of the same patient obtained at the same position of examination. These pairs of curves may be displayed on the CRT screen 20 immediately after the corresponding scan has taken place, and/or they may be plotted out on paper in the general form here shown, for a permanent record. Of course, the data itself may also be stored in digital form on a suitable record, e.g., magnetic disc or tape.

FIG. 14 includes three individual sub-figures, designated 14a, 14b and 14c, each showing data readings obtained from a different subject (person) under clinical conditions, the three sets of data being generally illustrative of different physiological conditions likely to be encountered in the general population. In these sub-figures, each vertical column represents data obtained from a different person, and each horizontal row shows data obtained at the same general location each of the three different individuals. In each individual graphical presentation there are separate traces or "curves" for each breast, the right breast data being shown in a darker, heavier line, and the left breast data being shown by a lighter, finer line, as indicated in the legend in the upper left-hand corner of the page (i.e., "Rt" and "Lt"). Each individual curve or trace represents composite detector output signals obtained at a different examination wavelength or, more particularly, at a particular step in the examination scan comprising one increment of the entire examination wavelength spectrum. In these graphical presentations, the ordinate represents detector output and wavelength is represented by the abscissa, although it is to be understood that such "detector output" comprises the intrinsic valuations referred to previously, involving compensation or conditioning based on nominal optical distance and the "near"-"far" data resolution described above. Also, the scale values for the ordinate and abscissa are not the same in the three different columns, the different curves having in effect been centered or partially centered in the available space for simplicity and uniformity in these drawings. Thus, in actual practice, different curves plotted on the same continuous and dimensionally consistent axes would show even greater differences for different patients since the location of some curves will be considerably different than others with respect to the particular position in the field defined by the ordinate and abscissa, depending upon the particular physiological conditions encountered in a given patient.

Considering the graphical representations of FIG. 14 in somewhat more detail, it will be noted that the two different tracings for the right and left breast, respectively, appear very symmetrical in the left column (FIG. 14a); indeed, the two traces are very nearly in registration with one another in almost all areas, apart from some magnitude differences in the top reading, obtained at the "inner" position (i.e., center of the breast and near the chest wall). Even so, the relative shape of the traces very much resemble one another, with the exception of some very slight divergence for the "outer" position (center of the breast and away from the chest wall) at the longer wavelengths. Some of the same general observations may be made with respect to the clinical data presented in the center column (FIG. 14b), although it will be noted that the two traces do not come into such close registration, and there are more differences in the shape of one curve compared to the other. These general characterizations are muchless true with respect to the data presented in the right-hand column (FIG. 14c), in which some readily apparent and significant divergence in curve shape is present, portions of the two different curves actually having oppositely-directed slopes of considerable steepness. Even from considering the curves in this rather superficial manner, and making even such generalized observations, it may not be surprising to learn that the actual patients involved were, in the case represented by columns 14a and 14b, relatively "normal" women of different ages and different breast composition (e.g., different amounts of glandular and/or fibrous connective tissue as compared to fat); in the case represented by column 14c, however, the data represents an older woman diagnosed medically as having certain breast abnormality or anomaly in each breast, of which that on the right side appeared more serious.

It is believed self-evident that consideration of the results indicated above demonstrates not only the presence of meaningful data but also the potential of a highly useful methodology. In this respect it is not the purpose of this specification to assert a complete, comprehensive and finalized description and explanation of all of the very complex physical and chemical factors involved in the propagation of light through living tissue, nor for every meaningful aspect of the data obtained by the method and apparatus disclosed; further, it is not intended to teach complete and definitive methodology for specific medical diagnosis. Instead, it is intended to show highly useful methods and apparatus for clinical examination and study of human subjects, and for presentation of the data so achieved, including comparative presentations for similar positions on different but analogous body portions of the same patient, and for a broad cross section of different patients at both the same and different ages, and also with respect to particular patients at various different points in their lifespan. Thus, while the invention contemplates the presence of clinically efficacious modalities which may be useful for many purposes perhaps including diagnosis of particular conditions and/or illness, it is presently contemplated that perhaps the most useful contribution of the invention is to provide a screening device and modality in which a familiar and therefore non-frightening medium (i.e., "light") is utilized in a harmless and noninvasive procedure made possible by relatively inexpensive apparatus operable by medical technicians as opposed to physicians themselves, primarily useful for indicating the need (or lack thereof) for much more intensive analytical investigation, i.e., mammography, ultrasound, biopsy, etc. In this respect, both the tabular-type form of data presentation and the graphical-type format are considered useful and, as already indicated, the tabular format may be made much more comprehensive and diverse than that set forth for purposes of illustration hereinabove. Particular advantage is asserted with respect to the methodology involved in and epitomized by the graphical presentations of FIG. 14, however, particularly with respect to the use of the different data-taking positions, the nature of the graphical format, and the comparative (paired) presentation.

It should be noted that the foregoing specification and appended drawings disclose concepts and methodologies principally described herein as applicable to study of the human female breast, but which are not at all limited to use for this purpose. That is, optical response and particularly spectral response data profiling in the manner described herein is definitely considered to be appropriate for, and valuable in, examination of other body portions, human or otherwise. While it may or may not be true that a given such application may call for slightly varying the specifics of the modality in actual application, the basic underlying concepts should nonetheless prove applicable and effective. Accordingly, the scope of this patent should be determined by consideration of the appended claims rather than with respect to specific attributes or parameters set forth above and/or in the attached drawings, describing and illustrating various preferred embodiments or characteristics, the scope of the claims to be determined through appropriate application of established principles of patent law including the doctrine of equivalents.

The embodiments of the invention in which an exclusive property or privilege is claimed are defined as follows:

1. Apparatus for obtaining optical response data from selected body portions of individual subjects indicative of the intrinsic internal physiological state of tissue within such body portions, comprising:
    a manually-manipulatable test instrument having at least first and second component members mounted for movement relative to one another and support means disposed therebetween for holding such members in selected mutually spaced relative positions;
    said first component member including light source means for emitting selected light from said first member;
    said first component member being adapted to fit closely against a selected body portion from which clinical data is desired to be obtained, in a manner to project said emitted light into the interior of such body portion;
    light-receiving means carried by at least said second component member for receiving at least part of the light projected into said selected body portion;
    said support means including position-variable elements for movement of one of said component members relative to the other to change the nominal optical distance between said source and said light-receiving means;
    means operatively coupled between said light source means and said light-receiving means for measuring the particular length of said nominal optical distance at various positions of said relative movement which effects change in such distance;
    and means for producing signals for computation representative of the nominal optical distance determined by said length-measurement means.

2. Apparatus for obtaining optical response data from selected body portions of individual subjects indicative of the intrinsic internal physiological state of tissue within such body portions, comprising:
    a manually-manipulatable test instrument having at least first and second component members and supportive guide means disposed therebetween for movably positioning such members in a plurality of differently-spaced but consistently-aligned relative positions;
    said first component member including light source means for emitting selected light from said first member;
    said first component member being adapted to fit closely against a selected body portion from which clinical data is desired to be obtained, so as to project said emitted light thereinto;
    light-receiving means carried by said second component member for receiving at least part of the light projected into said selected body portion;
    light-receiver means carried with said first component member at a known distance from said light source, for receiving certain of said light emitted by said source after projection thereof into said selected body portion and following reflection and back-scatter effects upon said light occurring within said body portion, such that the emitted and projected light is received at both a far point on said body portion spaced from that at which said light is introduced into the body portion and also at a near point spaced at least slightly less than the far point from the point at which the light is initially introduced to the body portion;
    said far and near points of light reception being separated by a particular optical distance determinable from the respective locations of such points and the nominal distances thereof from the point of light injection, and said apparatus including means for operatively determining a value for said particular optical distance.

3. Optical response apparatus according to claim 2 wherein said second component member includes first and second light-receiver means, said first light-receiver means being positioned generally along a first axis with respect to said light source and said second light-receiver means being spaced from the first light-receiver means so as to be positioned along a second and different axis with respect to said light source.

4. Optical response apparatus according to claim 3 wherein said second light-receiver means is disposed generally opposite and in general alignment with said light-receiver means carried with said first component member.

5. Apparatus according to claim 2 and including at least a pair of mutually cooperative light detectors associated with at least one of said component members, each having portions for receiving light wavelengths arriving at such component member from said source and through said body portion, and each of said detectors being adapted to provide electrical signals representative of at least certain of the light so received.

6. Apparatus according to claim 5 including at least a pair of said mutually cooperative light detectors associated with both of said component members to receive light from said source arriving at each component member after introduction into a body portion and undergoing reflection, scatter and transmission effects within said body portion.

7. Apparatus according to claim 6 wherein each of said mutually cooperative detectors in each such pair is of a type having specific differences from the other detector in that pair and effective at least in part over differing wavelength spectra.

8. Apparatus according to claim 6 wherein each of said mutually cooperative detectors in each such pair is of a type having specific differences from the other detector in that pair and effective at least in part over at least certain of the same wavelength spectra.

9. A method of obtaining optical response data from selected body portions of living beings indicative of the intrinsic internal physiological state of tissue within such body portions, comprising the steps of:

placing at least first and second optical probe members in optical engagement with different areas on the surface of the selected body portion in a manner effective to project light into and receive such light out of the interior of said body portion from between the optically-active portions of such probe members;

using position-fixing support means at least in part to hold said optical probe members in their said position of optical engagement, and determining the particular separation distance between said optically-active portions of said probe members while the latter are so held;

sending selected light from at least one of said probe member active portions into the selected body portion which is in optical engagement therewith, and receiving resulting light energy at least at the other probe member active portion;

quantifying and conditioning the said light energy received at said other probe member active portion by using said particular determined separation distance to condition such light energy data, for meaningful comparison with other such conditioned data obtained at other body portions and other separation distances.

10. The method of obtaining optical response data according to claim 9, and including the steps of moving said active portions of said first and second optical probe members from their said position of optical engagement with different areas on said selected body portion into other positions of optical engagement with the same body portion but at other locations thereon;

holding said optical probe members in position at such other locations while maintaining their said optical engagement there;

and repeating said steps of determining particular separation distance, sending selected light, receiving resulting light energy, and quantifying and conditioning received light energy by using the particular separation distance determinations to condition the light energy received at the other positions, for comparison with other such data.

11. The method of obtaining optical response data according to claim 10, wherein said selected body portion is the breast of a human female and said steps of placing the active portions of said optical probe members and obtaining conditioned data are carried out at a plurality of particular locations for an individual breast including at least one side portion thereof and generally centrally thereof.

12. The method of obtaining optical response data according to claim 11, wherein said step of placing said active portions of said optical probe members and obtaining data at a plurality of locations on the same breast includes at least a location generally centrally of the breast near the chest wall and a location generally centrally of the breast outward from the chest wall toward the nipple.

13. The method of obtaining optical response data according to claim 9, including the steps of receiving said resulting light energy from said body portion at a first location nearer that at which said selected light is sent into said body portion at said one optical probe member as compared to a second such location, as well as receiving said resulting light energy at said other optical probe member at a second location farther from that at which the light is sent into the body portion as compared to said first location, quantifying the resulting light energy received at said nearer location, and using at least said quantification of resulting light energy received at said nearer location as a conditioning factor for the quantifications of resulting light energy received at said second location, to condition the latter such quantifications for optical effects on the received light resulting from impingement of the light upon and passage thereof through the skin of the selected body portion at the place of light entry.

14. The method of obtaining optical response data according to claim 13, wherein said step of receiving resulting light at said location includes receiving such light at a point within not more than about two-to-three centimeters from the place at which said selected light is introduced to said selected body portion.

15. The method of obtaining optical response data according to claim 14, wherein said step of quantifying said resulting light received at at least one of said locations includes impinging such light upon two different types of light detector elements each having an active response over at least some of the same wavelengths.

16. A method of appraising the physiologic state o f selected body portions of living beings by optical response, comprising the steps of:

using at least first and second optical probe members to inject light into and receive injected light from the selected body portion at a plurality of predetermined different mutually-spaced positions thereon;

maintaining said optical probe members fixed in each of their said positions of physcial contact, and determining a measure of the nominal optical distance between said optically-active portions of said probe members while the latter are so maintained at each of said positions;

sending selected light spectra from at least one of said probe member active portions into the selected body portion and receiving resulting light energy at least at the other probe member active portion at each of said different positions, and producing corresponding valuations from the light energy so received at each such position;

using the said nominal optical distance measure determined at each such position to condition the light energy valuations produced for each such position;

and mutually comparing the conditioned light energy valuation data corresponding to the various different positions and different nominal optical distance measures which have been determined.

17. The method of optically appraising physiologic state as recited in claim 16, including the steps of sending selected wavelengths of said light into the selected body portion, correlating individual component parts of the said conditioned light energy valuation data obtained for individual instances of the said different optical probe positions with the particular selected ligh t wavelength for which such individual valuation data component parts are responsive and representative, and using such correlated valuation data component parts and particular selected wavelengths as the basis for said step of mutually comparing the conditioned light energy valuation data obtained at the various different positions and nominal optical distances which have been determined.

18. The method of optically appraising physiologic state as recited in claim 17, including the step of graphically plotting coordinates representative of at least certain of said correlated valuation data component parts and their corresponding wavelengths for different ones of said positions, and performing said step of mutually comparing by contrasting at least portions of one or more such graphical plots with others thereof.

19. The method recited in claim 17 as applied to human female breast anatomy, wherein said first and second optical probe members are placed generally opposite one another on the top and bottom surfaces of a breast, respectively, and periodically shifted from one to another predetermined location on said top and bottom surfaces, said one and another predetermined locations on said top and bottom breast surfaces comprising said plurality of different positions on the surface of the selected body portion.

20. The method as recited in claim 19, wherein said predetermined locations include at least one along the outer side portion of the breast and at least one generally centrally of that same breast.

21. The method as recited in claim 17 as applied to human female breast anatomy, including the steps of placing said first and second optical probe members in a plurality of particular different mutually-spaced positions with respect to each breast of the same human subject, with the said particular positions for one breast generally corresponding to those for the other;

holding said optical probe members in fixed position at each of such positions and establishing a measure of said nominal optical distance for each;

carrying on said steps of sending selected wavelengths of light and receiving resulting light energy at each of said plurality of particular positions for both breasts, and using the particular nominal optical distance established for each such position to condition the light energy valuation data produced for each such position;

and including the step of mutually comparing the conditioned light energy valuation data produced for various ones of said particular different positions on one breast with the conditioned data produced for the corresponding positions of the other breast.

22. The method as recited in claim 21, including the steps of correlating individual component parts of the said conditioned light energy valuation data for individual ones of the said different positions and nominal optical distances with the particular selected light wavelength for which such individual valuation data component parts are responsive and respresentative, and using such correlated valuation data component parts and particular selected wavelengths as the basis for said step of mutually comparing the conditioned light energy valuation data produced for the various different positions and different nominal optical distances.

23. The method as recited in claim 22, including the step of graphically plotting coordinates representative of at least certain of said correlated valuation data component parts and their respective wavelengths for selected corresponding positions on the two different breasts of the same human subject, said step of mutually comparing being carried out by contrasting at least portions of such graphical plots for at least one set of corresponding positions on opposite breasts of the same subject.

24. The method as recited in claim 23, wherein said step of graphically plotting coordinates is carried on for a plurality of sets of said selected corresponding positions on the two opposite breasts.

25. The method as recited in claim 24, wherein said step of graphically plotting coordinates is carried out at sets of corresponding positions on the two opposite breasts which include at least a first position located generally centrally of the breast and near the chest wall, and at least one other position located outwardly from said first position.

26. The method as recited in claim 25, wherein said other positions include one located generally centrally of the breast and outward and away from the chest wall, and another disposed along a marginal edge of the breast.

27. The method as recited in claim 16, and including the step of receiving said resulting light energy from said body portion at at least first and second locations which are disposed at different distances from the point where said light is sent into said body portion at said one optical probe member, one of said locations for receiving said resulting light energy being closer to the point where said light is sent into said body portion than the other such location, at least at certain of said different positions;

and using a representative valuation of said resulting light energy received at said closer location as a conditioning factor for producing conditioned valuations of said resulting light energy received at said other location, to condition the valuation data so produced for optical effects on the received light caused by impingement of the light upon and passage thereof through the skin of the selected body portion at the place of light entry, in addition to using the said nominal optical distance measure determined for the different optical probe positions to condition the valuation data produced for light energy received by said other optical probe member at such different positions.

28. The method as recited in claim 27, including the steps of sending selected wavelengths of said light into the selected body portion, correlating individual component parts of the said conditioned light energy data produced for individual instances of the said different optical probe positions with the particular selected light wavelength for which such individual data component parts are responsive and representative, and using such correlated data component parts and particular selected wavelengths as coordinates to graphically plot the conditioned light energy valuation data obtained at the various different positions and different nominal optical distances.

29. The method recited in claim 28 as applied to human female breast anatomy, wherein said first and second optical probe members are placed generally opposite one another on the top and bottom surfaces of a breast, respectively, and periodically shifted from one to another predetermined location on said top and bottom surfaces, said one and another predetermined locations on said top and bottom breast surfaces comprising said plurality of different positions on the surface of the selected body portion, said predetermined locations including at least one along the outer side portion of the breast and at least one generally centrally of that same breast.

30. The method as recited in claim 29, wherein said first and second optical probe members are placed in a plurality of particular different mutually-spaced positions with respect to each breast of the same human sunject and the said predetermined locations for one breast generally correspond to those for the other;
said optical probe members being held in fixed position at each of such locations and said nominal optical distance being determined for each;
said steps of sending selected wavelengths of light and receiving resulting light energy being carried out at each of said plurality of predetermined locations for both breasts, and the particular nominal optical distance determined for each such location being used to condition the light energy valuation data produced at each such position;
and including the step of mutually comparing the conditioned light energy data produced for various ones of said predetermined different locations for one breast with the conditioned data produced for the corresponding predetermined locations for the other breast.

31. The method as recited in claim 30, including the steps of correlating individual component parts of the said conditioned light energy data for individual ones of the said different locations and different nominal optical distances with the particular selected light wavelength for which such individual data component parts are responsive and representative, and using such correlated data component parts and particular selected wavelengths as the basis for said step of mutually comparing the conditioned light energy data produced for the various different locations and nominal optical distances.

32. The method as recited in claim 31, including the step of graphically plotting coordinates representative of at least certain of said correlated data component parts and their respective wavelengths for selected corresponding locations for the two different breasts of the same human subject, said step of mutually comparing being carried out by contrasting at least portions of such graphical plots for at least one set of corresponding locations for opposite breasts of the same subject.

33. The method as recited in claim 32, wherein said step of graphically plotting coordinates is carried on for a plurality of sets of said selected corresponding locations for the two opposite breasts.

34. The method as recited in claim 33, wherein said step of graphically plotting coordinates is carried out at sets of corresponding locations for the two opposite breasts which include at least a first location generally centrally of the breast and near the chest wall, and at least one other location located outwardly from said first location.

35. The method as recited in claim 34, wherein said other locations include one located generally centrally of the breast and outward and away from the chest wall, and another disposed along a marginal edge of the breast.

36. A method of appraising the physiologic state of selected body portions of living beings, comprising the steps of:
placing first and second optical probe members in operative light-injecting and receiving engagement with a selected body portion of each of a plurality of different living beings, at a selected location on each of said body portions
holding said first and second optical probe members fixed in each of their said locations of operative light-injecting and receiving engagement, and determining the nominal optical distance between optically-active portions of said probe members while the latter are so held in each of said locations;
sending selected light from at least one of said probe member active portions into the selected body portion with which it is in operative engagement, receiving resulting light energy at the other probe member active portion at each of said selected locations and determining representative light energy data for the light energy so received at each such different location;
using said determined nominal optical distance for each such location to condition the light energy data determined for that location;
receiving said resulting light energy from said body portion at a location nearer that at which said selected light is sent into said body portion at said one optical probe member than the location of said other optical probe member, at least at certain of said different selected locations;
using a representative valuation of said resulting light energy received at said nearer location as a conditioning factor for the said resulting light energy data determined for light received at said other optical probe member, to condition such data for optical effects on the received light resulting from impingement of the light upon and passage thereof into the selected body portion at the place of light entry, in addition to using the nominal optical distance determined for each of said certain optical probe locations to also condition the data for light energy received by said other optical probe member at such locations;

and mutually comparing the conditioned light energy data determined for the selected location on the selected body portion of one such living being with like conditioned data obtained at like locations on the like selected body portion of other such living individuals.

37. The method as recited in claim 36, wherein said step of mutually comparing the conditioned optical data from different living individuals is done by coordinating the data determined for a given such individual with respect to selected wavelengths of light sent into the selected body portion of that individual to which the data determinations correspond, and by comparing a given such data coordination from one such individual with other such data coordinations from other individuals.

38. The method as recited in claim 37, wherein said step of comparing a given such data coordination with others thereof comprises comparing the coordinated data determinations for a selected body portion of a particular one such living individual with a composite data coordination prepared by combining data determinations made for the same selected body portion of a plurality of different living individuals.

39. An optical probe for use in apparatus for obtaining physiological condition data from selected body portions of individual subjects, comprising:

a generally rigid body defining a laterally-enclosed internal space and having a generally tubular nosecone at a forward end adapted to contact said selected body portions in light-sealing relation, a generally planar partition member disposed diametrically across said nosecone at a position spaced inward from the end extremity thereof, thereby walling off said internal space and providing a projecting tubularly-enclosed area;

a septum extending forwardly from said partition member and dividing said tubularly-enclosed area;

said nosecone, partition member and septum being substantially impervious to infrared and near infrared light, and having surfaces within said tubularly-enclosed area of diffusely-reflecting material;

at least one light-detector means disposed at least partially within said tubularly-enclosed area and adjacent said septum;

and signal-carrying cable means coupled to said light-detector means for transmitting light-reception signals therefrom, said cable means extending out of said body.

40. The optical probe as defined in claim 39, and including a light source disposed at least partially within said tubularly-enclosed area and arranged to emit light out from the forward end of said nosecone, said light source being located on the opposite side of said septum from said light-detector means.

41. The optical probe as defined in claim 39, and including a pair of light-detector elements on at least one side of said septum and at least partially within said tubular area.

42. The optical probe as defined in claim 39, and including light-detector means located on both sides of said septum and at least partially within said tubularly-enclosed area.

43. The optical probe as defined in claim 42, and including a pair of light-detector elements on at least one side of said septum and at least partially within said tubular area.

44. The optical probe according to claim 43, wherein said pair of light-detector elements includes two different types of detectors.

45. The optical probe according to claim 40, and including an optical mask element disposed diametrically across said tubular nosecone forwardly of said partition and spaced therefrom; said mask enclosing said light-detector means between the mask, the partition and the tubular nosecone;

said source and mask being adapted to emit light from said source through and beyond said mask.

46. The optical probe according to claim 45, wherein said mask includes a light-transmissive portion aligned with said detection means for admitting light through the mask and to such detection means.

47. The optical probe according to claim 46, wherein said light-transmissive portion comprises an aperture extending through the mask, and wherein said aperture is arcuate in form and concave with respect to a light source which is disposed across the septum from the light-detection means.

* * * * *

UNITED STATES PATENT AND TRADEMARK OFFICE
CERTIFICATE OF CORRECTION

PATENT NO. : 4,570,638

DATED : February 18, 1986

INVENTOR(S) : Hugh F. Stoddart and Gary D. Lewis

It is certified that error appears in the above-identified patent and that said Letters Patent is hereby corrected as shown below:

On the patent cover, column 2, delete the EXEMPLARY CLAIM and insert the following:

-- ABSTRACT OF THE DISCLOSURE

Methodology and apparatus for the clinical evaluation of biological matter, in particular the human breast, in situ and in vivo, by spectral light transmissivity. An optical probe introduces selected light spectra into the examination subject at a first position and resulting light is detected at a second position located some distance from the infusion point; also, reception preferably occurs at another location, and the distances of these locations from the infusion point are determined. The light energy received at the distant points is quantified and conditioned by use of the determined distances from the infusion point and also by contrasting the data from the two differently-located reception points, such that the resulting data is compensated or normalized to characterize intrinsic internal tissue characteristics in an absolute sense, devoid of individual characteristics such as skin pigmentation, breast thickness, etc. The methodology further includes analytical or diagnostic treatment of the conditioned data by specific comparison of conditioned data taken from different regions of the same subject, of conditioned data taken from the same region on physiologically paired and/or different subjects, and also provides for meaningful accumulation of large-scale "background" or "average" values based upon identified and selected patient populations. --

UNITED STATES PATENT AND TRADEMARK OFFICE
CERTIFICATE OF CORRECTION

PATENT NO. : 4,570,638

DATED : February 18, 1986

INVENTOR(S) : Hugh F. Stoddart and Gary D. Lewis

It is certified that error appears in the above-identified patent and that said Letters Patent is hereby corrected as shown below:

Column 1, line 26:
    "amont" should be -- among --.

Column 2, lines 22 and 23
    "diagnosis" should be -- diagnostic --.

Column 2, lines 66 and 67:
    "inclusive" should be -- exclusive --.

Column 5, line 48 (second occurrence):
    "relative" should be -- relatively --.

Column 6, line 39:
    "extend" should be -- extent --.

Column 7, line 18:
    "om" should be -- in --.

Column 7, line 43:
    "whichare" should be -- which are --.

Column 7, line 44:
    "breflected" should be -- reflected --.

Column 9, line 8:
    "uitilized" should be -- utilized --.

Column 9, line 53:
    "preferably" should be -- preferable --.

Column 9, line 68:
    "aout" should be -- about --.

UNITED STATES PATENT AND TRADEMARK OFFICE
CERTIFICATE OF CORRECTION

PATENT NO. : 4,570,638

DATED : February 18, 1986

INVENTOR(S) : Hugh F. Stoddart and Gary D. Lewis

It is certified that error appears in the above-identified patent and that said Letters Patent is hereby corrected as shown below:

Column 10, line 29:
 "1.0-1.3 microns" should be -- 1.0-1.1 microns, 1.2-1.3 microns, --.

Column 10, line 39:
 after "since" insert -- the --.

Column 11, line 58:
 "substracted" should be -- subtracted --.

Column 21, line 26:
 "said" should be -- such --.

Column 22, line 52, Claim 14, line 3:
 after "said" insert -- nearer --.

Column 25, line 38, Claim 30, line 5:
 "sunject" should be -- subject --.

Column 26, line 33, Claim 36, line 8:
 after "portions" insert -- ; --.

Signed and Sealed this

Twenty-second Day of July 1986

[SEAL]

Attest:

DONALD J. QUIGG

Attesting Officer

Commissioner of Patents and Trademarks